United States Patent
Fenniri

(12) 
(10) Patent No.: US 6,696,565 B2
(45) Date of Patent: Feb. 24, 2004

(54) METHOD AND ASSOCIATED PYRIMIDO[4,5-D]PYRIMIDINE-2,5-DIONES AND PYRIDO[4,3-D]PYRIMIDIN-2-ONES FOR FORMING NANOTUBES

(75) Inventor: Hicham Fenniri, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 53 days.

(21) Appl. No.: 10/050,292

(22) Filed: Jan. 16, 2002

(65) Prior Publication Data

US 2002/0151556 A1 Oct. 17, 2002

Related U.S. Application Data

(60) Provisional application No. 60/262,385, filed on Jan. 17, 2001.

(51) Int. Cl.[7] .................... C07D 487/04; C07D 471/04
(52) U.S. Cl. ................ 544/244; 544/256; 544/279
(58) Field of Search ................ 544/244, 256, 544/279

(56) References Cited

U.S. PATENT DOCUMENTS 5,753,088 A    5/1998 Olk ...................... 204/173

OTHER PUBLICATIONS

Hicham Fenniri et al., "Helical Rosette Nanotubes: Design, Self–Assembly, and Characterization", J. Am. Chem. Soc. 2001, pp. 3854–3855, (BNSDOCID: XP–002205672).

Hicham Fenniri et al., "Towards Self–Assembled Electro- and Photo–Active Organic Nanotubes", Polymer Preprints 2001, 42(2), pp. 569–570, (BNSDOCID: XP–001087749).

George M. Whitesides et al., "Noncovalent Synthesis: Using Physical—Organic Chemistry To Make Aggregates", Acc. Chem. Res., vol. 28, No. 1, 1995, pp. 37–44.

Sergei V. Kolotuchin et al., "Self–Assembly Mediated by the Donor—Donor—Acceptor•Acceptor—Acceptor—Donor (DDA•AAD) Hydrogen–Bonding Motif: Formation of a Robust Hexameric Aggregate", J. Am. Chem. Soc., vol. 120, No. 35, 1998, pp. 9092–9093.

Rosa E. Melendez et al., "Hydrogen–Bonded Ribbons, Tapes and Sheets as Motifs for Crystal Engineering", Springer Link: Topics in Current Chemistry—Abstract vol. 198 (1998), 2 pgs. Abstract only.

Scott L. Forman et al., "Toward Artificial Ion Channels: A Lipophilic G–Quadruplex", J. Am. Chem. Soc., vol. 122, No. 17, 2000, pp. 4060–4067.

(List continued on next page.)

Primary Examiner—Mukund J. Shah
Assistant Examiner—Thomas McKenzie
(74) Attorney, Agent, or Firm—Barnes & Thornburg

(57) ABSTRACT

A method and associated compounds for forming nanotubes are disclosed. Examples of such compounds include those having the formula:

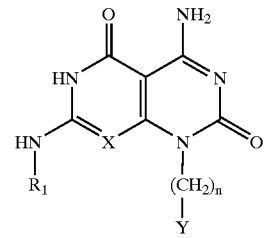

wherein X is CH or nitrogen; n is an integer of, 1, 2, 3, or 4; Y is an amino acid having an amino group covalently bound to an α-carbon of said amino acid and said amino group is covalently bound to a carbon of the $(CH_2)_n$ group; and $R_1$ is aliphatic; and salts thereof.

35 Claims, 13 Drawing Sheets

OTHER PUBLICATIONS

Giovanni Gottarelli et al., "The Self-Recognition and Self-Assembly of Folic Acid Salts in Isotropic Water Solution", Helvetica Chemica Acta—vol. 79 (1996), pp. 220–234.

Harm-Anton Klock, et al., "Self-Assembly of Rodlike Hydrogen-Bonded Nanostructures", J. Am. Chem. Soc., vol. 121, No. 30, 1999, pp. 7154–7155.

Nobuo-Kimizuka et al., "Mesoscopic Supramolecular Assembly of a 'Janus' Molecule and a Melamine Derivative via Complementary Hydrogen Bonds", J. Chem. Soc., Chem. Commun., 1995, pp. 2103–2104.

Toyoko Imae et al., "Formation of Fibrous Molecular Assemblies by Amino Acid Surfactants in Water", J. Am. Chem. Soc., vol. 114, No. 9, 1992, pp. 3414–3419.

David A. Frankel et al., "Supramolecular Assemblies of Diacetylenic Aldonamides", J. Am. Chem. Soc., vol. 116, No. 22, 1994, pp. 10057–10069.

Jürgen-Hinrich Fuhrhop et al., "Molecular Monolayer Rods and Tubules Made of α–(L–Lysine), ω–(Amino) Bolaamphiphiles", J. Am. Chem. Soc., vol. 115, No. 4, 1993, pp. 1600–1601.

Joe M. Schnur, "Lipid Tubules: A Paradigm for Molecularly Engineered Structures", Science, vol. 262, Dec. 10, 1993, pp. 1669–1676.

Naotoshi Nakashima et al., "Optical Microscopic Study of Helical Superstructures of Chiral Bilayer Membranes", J. Am. Chem. Soc. 1985, 107, pp. 509–510.

Jacque H. Georger et al., "Helical and Tubular Microstructures Formed by Polymerizable Phosphatidylcholines", J. Am. Chem. Soc., vol. 109, No. 20, 1987, pp. 6169–6175.

Nasreen G. Chopra et al., "Boron Nitride Nanotubes", Science, vol. 269, Aug. 18, 1995, pp. 966–967.

Tomoko Kasuga et al., "Formation of Titanium Oxide Nanotube", Langmuir, vol. 14, No. 12, 1998, pp. 3160–3163.

Wayne Shenton et al., "Inorganic–Organic Nanotube Composites from Template Mineralization of Tobacco Mosaic Virus", Wiley InterScience Article Abstract, Online ISSN: 1521–4095, Print ISSN: 0935–9648, Advanced Materials, vol. 11, Issue 3, 1999, 2 pgs. Abstract only.

Charles J. Brumlik et al., "Template Synthesis of Metal Microtubules", J. Am. Chem. Soc., vol. 113, No. 8, 1991, pp. 3174–3175.

Ewan J. M. Hamilton et al., "Preparation of Amorphous Boron Nitride and Its Conversion to a Turbostratic, Tubular Form", Science, vol. 260, Apr. 30, 1993, pp. 659–661.

Sumio Lijima, "Helical microtubules of graphitic carbon", Nature, vol. 354, Nov. 7, 1991, pp. 56–58.

Maarten F. M. Roks et al., Biomimetic Macromolecular Chemistry: Design and Synthesis of an Artificial Ion Channel Based on a Polymer Containing Cofacially Stacked Crown Ether Rings. Incorporation in Dihexadecyl Phosphate Vesicles and Study of Cobalt Ion Transport, Macromolecules, vol. 25, No. 20, 1992, pp. 5398–5407.

Akira Harada, "Synthesis of a tubular polymer from threaded cyclodextrins", Nature, vol. 364, Aug. 5, 1993, pp. 516–518.

Naomi Sakai et al., "Transmembrane B–DNA", Short Communications, Chembiochem 2000, No. 2, pp. 123–125.

Peter R. Ashton et al., "Synthetic Cylic Oligosaccharides—Syntheses and Structural Properties of a Cyclo1→4)–α–L–rhamonopyranosyl–[1→4)–α–D–mannopyranosyl]trioside and –tetraoside**", Chem. Eur. J. 1996, 2, No. 5, pp. 580–591.

James C. Nelson, "Solvophobically Driven Folding of Nonbiological Oligomers", Science, vol. 277, Sep. 19, 1997, pp. 1793–1796.

M. Reza Ghadiri et al., "Self–assembling organic nanotubes based on a cyclic peptide architecture", Nature, vol. 366, Nov. 25, 1993, pp. 324–327.

Mark Mascal et al., "The G—C DNA Base Hybrid: Synthesis, Self–Organization and Structural Analysis", J. Org. Chem. vol. 64, No. 23, 1999, pp. 8479–8484.

Andrew Marsh et al., "Self–complementary hydrogen bonding heterocycles designed for the enforced self–assembly into supramolecular macrocycles", Chem. Commun., 1996, pp. 1527–1528.

M. Mascal et al., "Programming a Hydrogen–Bonding Code for the Specific Generation of a Supermacrocycle", Angew. Chem. Int. Ed. 1996, vol. 35, pp. 2204–2206.

A. Marsh et al., "Self–complemetnary hydrogen bonding heterocycles designed for the enforced self–assembly into supramolecular macrocycles", Chem. Commun. 1996, pp. 1527–1528.

R. E. Meléndez et al., "Hydrogen–Bonded Ribbons, Tapes and Sheets as Motifs for Crystal Engineering", Top. Curr. Chem. 1998, vol. 198, pp. 97–129.

T. C. Marsh et al., "A new DNA nanostructure, the G–wire, imaged by scanning probe microscopy", Nucleic Acids. Res. 1995, vol. 23, pp. 696–700.

S. Lahiri et al., "Solvophobically Driven π–Stacking of Phenylene ethynylene Macrocycles and Oligomers", J. Am. Chem. Soc. 2000, vol. 122, pp. 11315–11319.

W. Shenton et al., "Inorganic—Organic Nanotube Composites from Template Mineralization of Tobacco Mosaic Virus", Adv. Mater 1999, vol. 11, pp. 253–256.

C. R. Cantor et al., "Structures of nucleic acids", Biophysical Chemistry, Freeman: New York, 1980.

J. H. K. K. Hirschberg et al., "Helical self–assembled polymers from cooperative stacking of hydrogen–bonded pairs", Nature 2000, vol. 407, pp. 167–170.

K. C. Russell, et al., "Investigation of Self–Assembled Supramolecular Species in Solution by IL–ESMS, a New Mass Spectrometric Technique", Angew Chem. Int. Ed. Engl. 1995, vol. 34, No. 2, pp. 209–213.

X. Chang et al., "Characterization of Hydrogen–Bonded Aggregates in Chloroform by Electrospray Ionization Mass Spectrometry", J. Org. Chem. 1996, vol. 61, pp. 2204–2206.

K. A. Jolliffe et al., "Characterization of Hydrogen–Bonded Supramolecular Assemblies by MALDI–TOF Mass Spectrometry after AG+ Labeling", Angew. Chem., Int. Ed. 1998, vol. 37, pp. 1247–1251.

S. L. Mayo et al., "DREIDING: A Generic Force Fields for Molecular Simulations", J. Phys. Chem. 1990, vol. 94, pp. 8897–8909.

D. N. Chin et al., "Computations and H NMR Spectroscopy of the Imide Region Can Distinguish Isomers of Hydrogen–Bonded Aggregates", J. Org. Chem. 1997, vol. 62, pp. 1891–1895.

METHOD AND ASSOCIATED PYRIMIDO[4,5-D]PYRIMIDINE-2,5-DIONES AND PYRIDO[4,3-D]PYRIMIDIN-2-ONES FOR FORMING NANOTUBES

CROSS-REFERENCE TO RELATED APPLICATION

This application claims the benefit of the filing date of Application Serial No. 60/262,385 filed Jan. 17, 2001, titled METHOD AND ASSOCIATED COMPOUNDS FOR FORMING NANOTUBES.

GOVERNMENT RIGHTS

Research relating to this invention was supported in part by the U.S. Government under Grant No. CHE-9875390 awarded from the National Science Foundation. The U.S. Government may have certain rights in this invention.

BACKGROUND OF THE INVENTION

The present invention generally relates to a method and associated compounds for forming nanotubes. The present invention particularly relates to a method and associated compounds for the hierarchical self-assembly of organic nanotubes from self-assembled supermacrocycles.

Nanotubes can be thought of as long, thin cylinders of carbon which are unique for their size, shape, and physical properties. For example, nanotubes are extremely strong, low weight, stabile, flexible, have good heat conductance, and have a large surface area. In addition, nanotubes possess a host of intriguing electronic properties. The aforementioned properties of nanotubes has lead to an intense investigation of utilizing these structures in the fields of materials science, nanotechnology, molecular electronic and photonic devices, sensor and artificial channel systems.

The particular the properties a nanotube possesses is dependent upon several factors including its diameter, length, chemical make up, and chirality. Therefore, the ability to produce nanotubes which have particular desirable properties is dependent upon being able to form or synthesize nanotubes which have, for example, a certain length. Unfortunately, prior to the present invention, the synthetic schemes for conveniently and efficiently producing nanotubes possessing a wide range of specific desirable characteristics have been extremely limited.

Therefore, in light of the above discussion, it is apparent that what is needed is a method an associated compounds for forming nanotubes that addresses the above discussed drawback of nanotube synthetic schemes.

SUMMARY OF THE INVENTION

In accordance with one embodiment of the present invention, there is provided a compound having the formula:

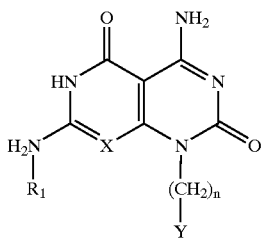

wherein X is carbon or nitrogen; n is an integer of, 1, 2, 3, or 4; Y is an amino acid having an amino group covalently bound to an α-carbon of the amino acid and the amino group is covalently bound to a carbon of the $(CH_2)_n$ group; and $R_1$ is aliphatic; and salts thereof.

In accordance with another embodiment of the present invention, there is provided a compound having the formula:

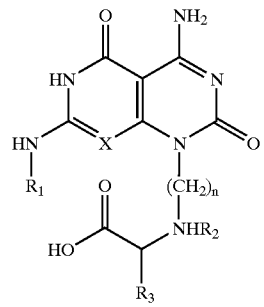

wherein X is carbon or nitrogen; n is an integer of 1, 2, 3, or 4; $R_1$ is aliphatic; $R_2$ is hydrogen; and $R_3$ is —$CH_3$, —$CH_2OH$, —$CH_2CH_2SCH_3$, —$CH_2CO_2H$, —$CH_2CH(CH_3)_2$, —$CH_2C_6H_5$, —$CH_2$-p-$(OH)C_6H_4$, —$CH_2CH_2CH_2CH_2NH_2$, or $R_2$ and $R_3$ together form

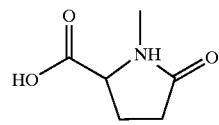

and salts thereof.

In accordance with yet another embodiment of the present invention, there is provided a method of forming a nanotube. The method includes disposing a compound having the formula

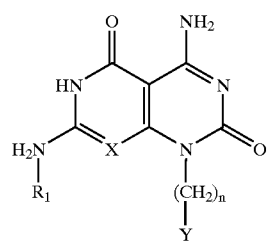

or salts thereof in a solution at a sufficient concentration so that the nanotube is formed, wherein X is carbon or nitrogen; n is an integer of, 1, 2, 3, or 4; Y is an amino acid having an amino group covalently bound to an α-carbon of the amino acid and the amino group is covalently bound to a carbon of the $(CH_2)_n$ group; and $R_1$ is aliphatic.

In accordance with still another embodiment of the present invention, there is provided a method of forming a nanotube. The method includes disposing a compound having the formula

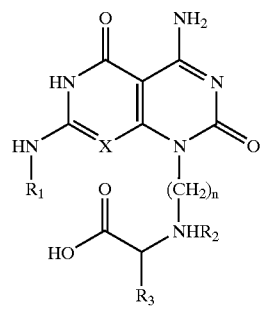

or salts thereof in a solution at a sufficient concentration so that the nanotube is formed, wherein X is carbon or nitrogen;

n is an integer of 1, 2, 3, or 4; $R_1$ is aliphatic; $R_2$ is hydrogen; and $R_3$ is —$CH_3$, —$CH_2OH$, —$CH_2CH_2SCH_3$, —$CH_2CO_2H$, —$CH_2CH(CH_3)_2$, —$CH_2C_6H_5$, —$CH_2$-p-(OH)$C_6H_4$, —$CH_2CH_2CH_2CH_2NH_2$, or $R_2$ and $R_3$ together form

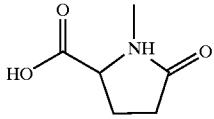

In accordance with still another embodiment of the present invention there is provided a compound having the formula:

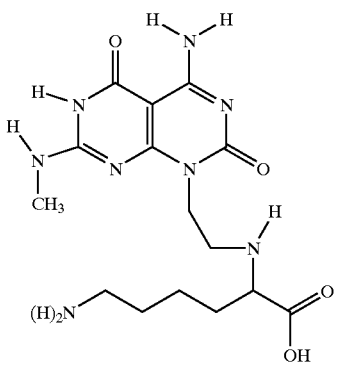

and salts thereof.

In accordance with still another embodiment of the present invention there is provided a method of forming a nanotube. The method includes disposing a compound having the formula

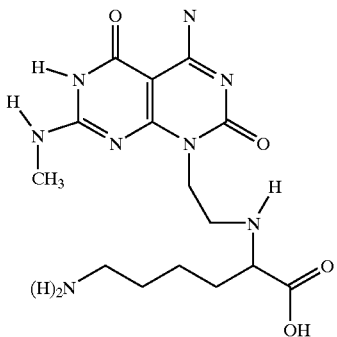

in a solution at a sufficient concentration so that the nanotube is formed.

In accordance with still another embodiment of the present invention there is provided a nanotube which includes molecules having the formula

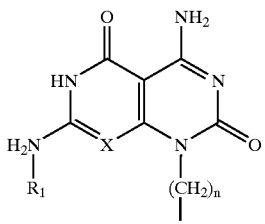

wherein X is carbon or nitrogen; n is an integer of, 1, 2, 3, or 4; Y is an amino acid having an amino group covalently bound to an α-carbon of the amino acid and the amino group is covalently bound to a carbon of the $(CH_2)_n$ group; and $R_1$ is aliphatic; and salts thereof, and a number of the molecules are arranged relative to one another so as to form a supermacrocycle.

It is therefore an object of the present invention to provide new and useful compounds for forming nanotubes.

It is another object of the present invention to provide improved compounds for forming nanotubes.

It is still another object of the present invention to provide a new and useful method for forming nanotubes.

It is yet another object of the present invention to provide an improved method for forming nanotubes.

It is still another object of the present invention to provide a new and useful nanotube.

It is yet another object of the present invention to provide an improved nanotube.

The above and other objects, features, and advantages of the present invention will become apparent from the following description and attached drawings.

DETAILED DESCRIPTION OF THE PREFERRED EMBODIMENT

Figure 1:
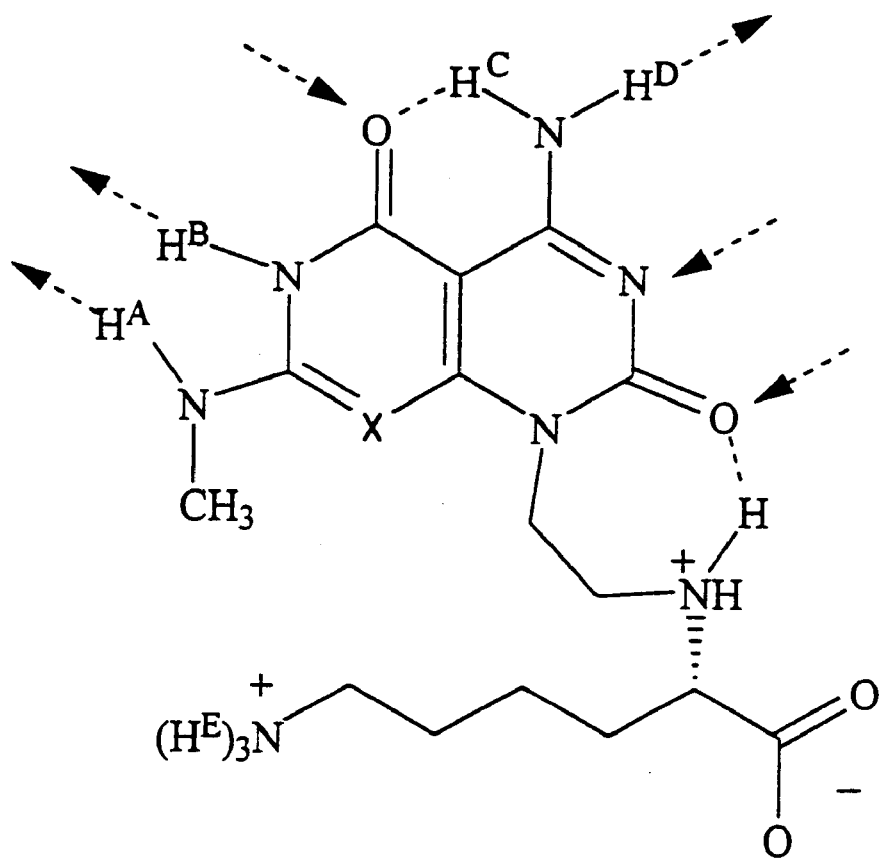
FIG. 1 is a representation of a compound of the present invention.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

For a system based on hydrogen bonds to self-assemble in water one has to balance the enthalpic loss (H-bonds) with a consequent entropic gain (stacking interactions and hydrophobic effect). If preorganized, ionic H-bonds could also add to the enthalpic term. With this in mind, the compound shown in FIG. 1 (hereinafter referred to as L-module 1) was designed and synthesized with the following features (i) a hydrophobic base unit possessing the Watson-Crick donor-donor-acceptor (DDA) H-bond array of guanine and (ii) the acceptor-acceptor-donor (AAD) H-bond array of cytosine. Note that arrows pointing away from the molecule denote a donor and the arrows pointing toward the molecule denote an acceptor. A carbon or a nitrogen atom can be inserted at the position denoted by X in L-module 1. An appropriate counter ion for L-module 1, or other modules, can be for example $CF_3CO_2^-$. Furthermore, a methyl group ($^4HNCH_3$) was introduced into the structure of L-module 1 so as to minimize the peripheral access of water and enforce the formation of an intramolecular ionic hydrogen bond between the side chain secondary ammonium and the neighboring ring carbonyl (see FIG. 1). However, it should be understood that other bulky hydrophobic groups can be utilized in the present invention, including but not limited to other aliphatic or alkyl groups, as long as they perform the aforementioned function, i.e. minimize the peripheral access of water and enforce the formation of an intramolecular ionic hydrogen bond, and do not interfere with the formation of the nanotube. In addition, an ethylene spacer unit linking the base component to the chiral center was chosen in order to allow for the intramolecular ionic H-bond (see FIG. 1). It should be appreciated that other spacer units, including but not limited to 1, 3, and 4 carbon atom spacers, can be utilized in the present invention as long as they allow for the aforementioned intramolecular ionic H-bond and do not interfere with nanotube formation. An amino acid moiety that dictates the supramolecular chirality of the resulting assembly is covalently bound to the spacer unit as shown in FIG. 1. Any amino acid, including the stereoisomers thereof, can be utilized as long as it does not interfere with nanotube formation. For example, amino acids which may be used in the present invention include, but are not limited to, alanine, arginine, asparagine, aspartate, cysteine, glutamine, glutamate, glycine, histidine, isoleucine, leucine, lysine, methionine, phenylalanine, proline, serine, threonine, tryptophan, tyrosine, valine, hydroxyproline, γ-carboxyglutamate, or o-phosphoserine.

Figure 2A:
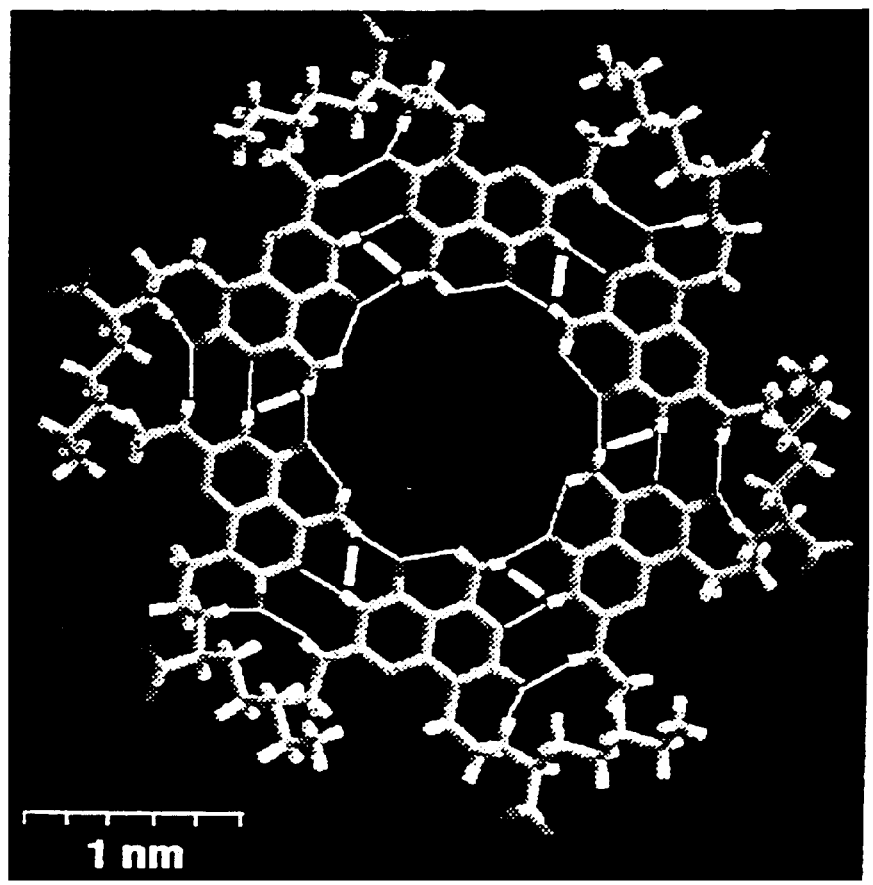
FIG. 2A is a molecular model of a supermacrocycle formed from the compound shown in FIG. 1.
Figure 2B:
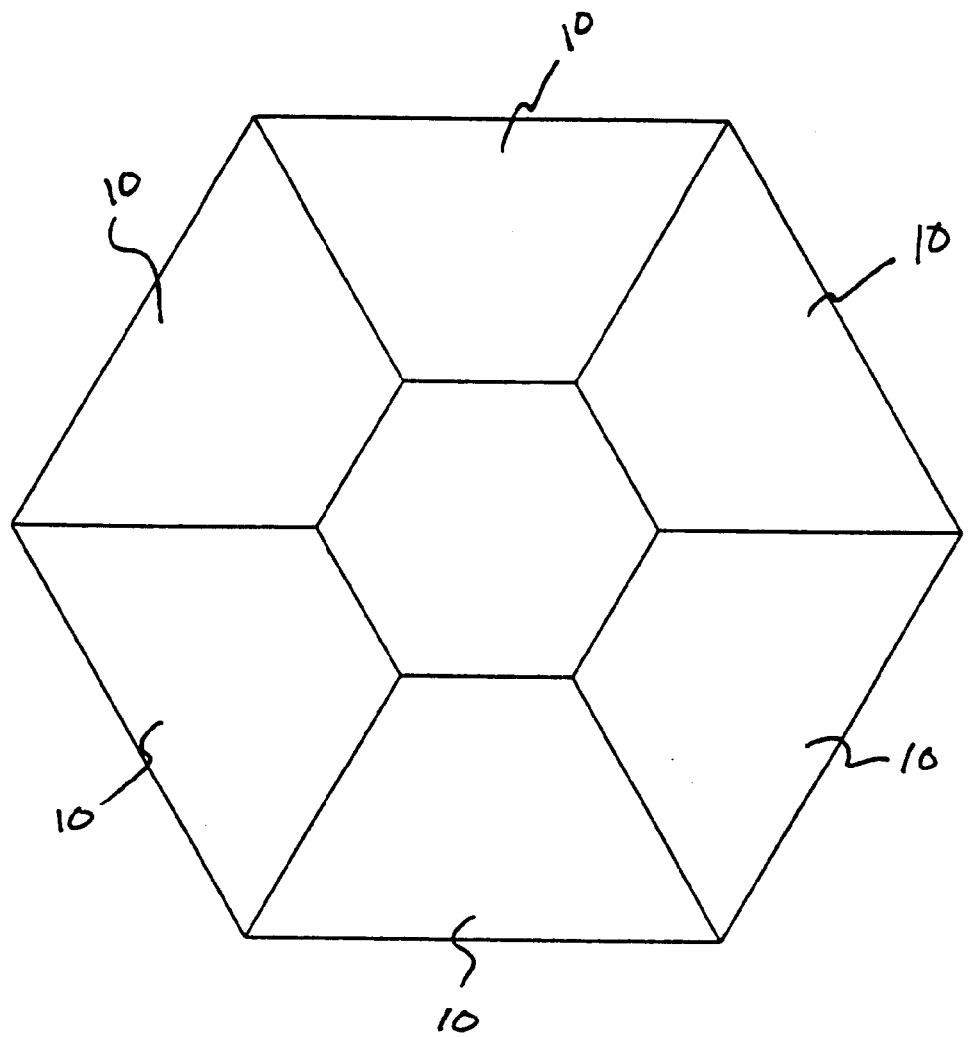
FIG. 2B is a schematic representation of the supermacrocycle shown in FIG. 2A.

It should be appreciated that modules (i.e. molecules) which possess the above described characteristics will self-assemble into supermacrocycles or discrete nanotubular assemblies in water or aqueous solutions. Supermacrocycles are defined herein as being a number of organic molecules covalently or noncovalently bound together so as to form a ring structure. For example, as shown in FIGS. 2A and 2B, one supermacrocycle these compounds will self-assemble into is a 6-mer. Note that FIG. 2A is a molecular model of the supermacrocycle L-module 1 self-assembles into, while FIG. 2B schematically depicts the supermacrocycle L-module 1 self-assembles into with each trapezoid 10 representing one L-module 1 molecule. With respect to FIG. 2A the thin lines represent the hydrogen bond network and the thick lines highlight unique intermodular NOE's which are discussed in greater detail below.

Figure 3:
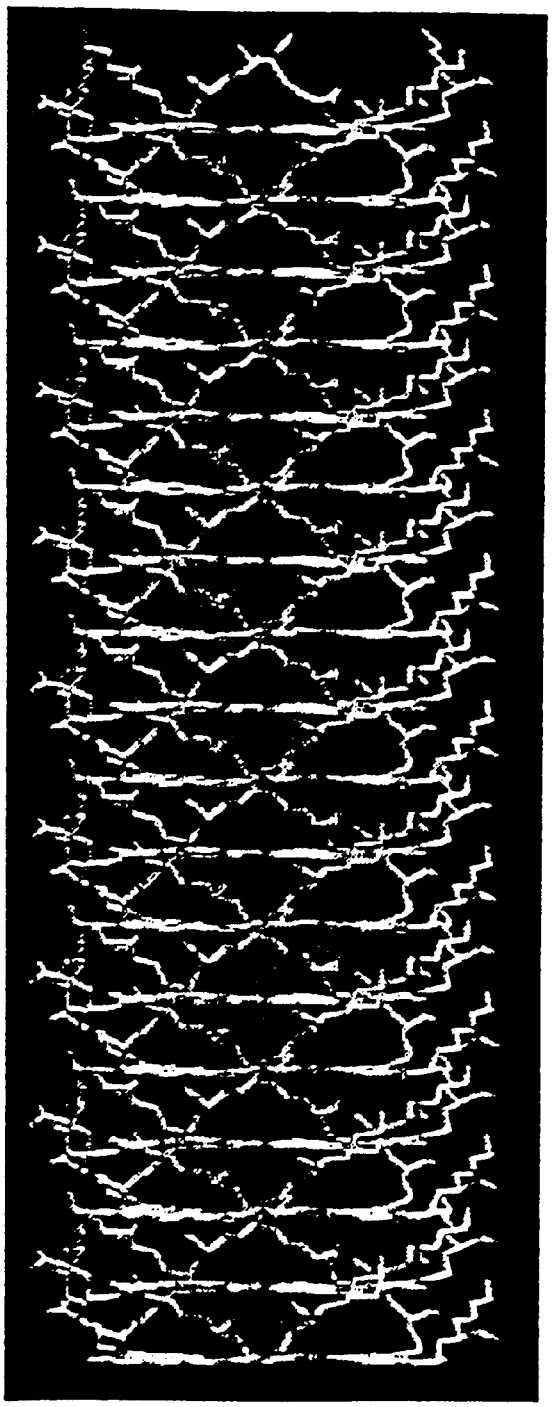
FIG. 3 is a molecular model of a nanotube formed from supermacrocycles of FIG. 2A.

It should be appreciated that the process of forming nanotubes with the modules of the present invention is hierarchical. In particular, what is meant by hierarchical is that the modules of the present invention first self-assembly into the above discussed supermacrocycles, and then the supermacrocycles self-assembly into nanotubes. For example, one nanotube assembly L-module 1 could self-assembly into is shown by way of a molecular model in FIG. 3. In particular, FIG. 3 shows 18 supermacrocycles arranged in a tubular fashion with a starting interplane distance of 4.5 angstroms.

It should also be appreciated that the ability of the modules of the present invention to self-assembly into supermacrocycles or discrete nanotubular assemblies in water or aqueous solutions is unique in several respects. For example, other compounds and methods for forming nanotubes require the formation of supermacrocyclic assemblies in organic solvents, and in solid and liquid crystalline states. Being able to form soluble nanotubular assemblies in water or aqueous solutions is an advantage of the present invention since it enhances the ease with which the nanotubes can be synthesized. In addition, having soluble nanotubular assemblies enhances the ability to utilize the nanotubes in other applications, e.g. photonic devices.

Figure 4A:
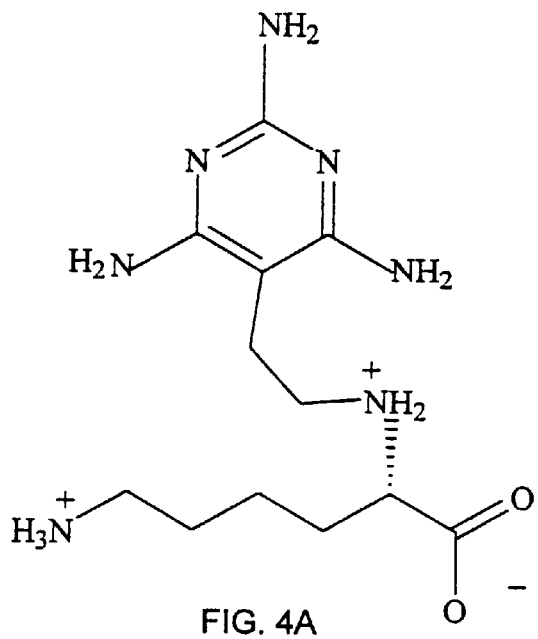
FIG. 4A is a representation of another compound of the present invention.
Figure 4B:
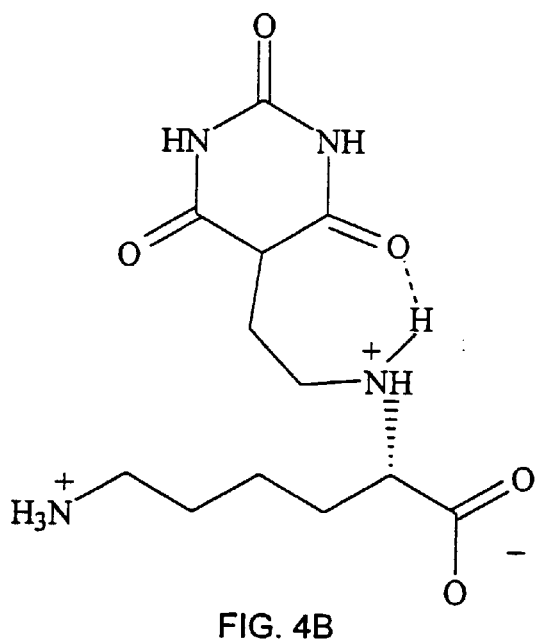
FIG. 4B is a representation of still another compound of the present invention.
Figure 4C:
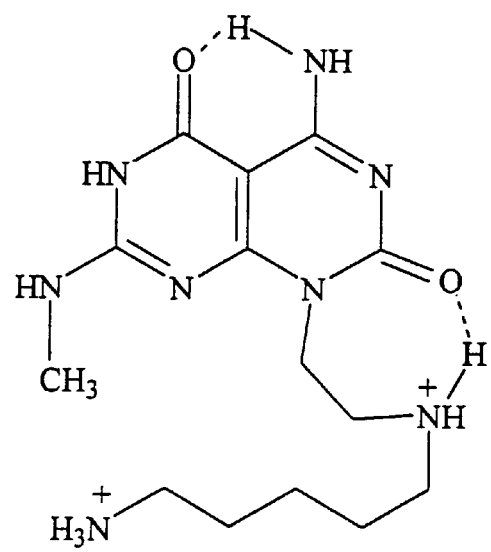
FIG. 4C is yet another representation of a compound of the present invention.

The following is a general synthetic strategy (i.e. schemes 1–4) which allows oligomerization and functionalization at virtually any position of a module (i.e. molecule) having the above discussed design characteristics. In particular, these schemes were utilized to synthesize D and L-module 1 and modules 2, 3, and 4 which are shown in FIGS. 4A, 4B, and 4C, respectively. However, it should be understood that this strategy can be extended to the preparation of other modules. In particular, the strategy is amenable to oligomerization using standard peptide synthesis chemistry, thereby allowing the formation of nanotubular assemblies with, for example, predetermined dimensions.

The abbreviations used in each scheme of the synthetic strategy are as follows: Bn (benzyl); Boc (tert-butyloxycarbonyl); Cbz (benzyloxycarbonyl); DCC (dicyclohexylcarbodiimide); 1,2-DCE (1,2-dichloroethane); $dH_2O$ (deionized NanoPure water); DIEA (diisopropylethylamine); DMAP (4-N,N-dimethylaminopyridine); DME (1,2-dimethoxyethane) DMF (dimethylformamide); EtOH (ethanol); $Et_3N$ (triethylamine); h (hour); $NaB(OAc)_3H$ (sodium triacetoxyborohydride); NMMO (N-methylmorpholine N-oxide); p-TsOH (para-toluenesulfonic acid); rt (room temperature); TFA (trifluoroacetic acid); TFAA (trifluoroacetic anhydride); and THF (tetrahydrofuran).

All the new compounds were characterized by $^1H$ and $^{13}C$-NMR, and MS. High resolution MS and elemental analysis were obtained for key intermediates and final products. In all the cases the analytical data was in agreement with the structures. Note that each compound is assigned a reference number, e.g. 1, 2, 3 and so on, or a letter and a number, e.g. L-17 and so on, which is utilized to identify the compound in the synthetic strategy. Also note that any compound referenced but not specifically shown in the general synthetic strategy is discussed below with respect to a more detailed discussion of the synthesis of the compounds. Compounds 2, 17, 19, and 26–28 were prepared according to the reported procedures set forth in Yoneda, Chem. Soc. Perkin Trans. 1 1976, 16, 1805–1808; Krapcho, Synth. Commun. 1990, 20, 2559–2564; Husbands, J. Med. Chem. 1999, 42, 4446–4455; and Ishikawa, Chem. Pharm. Bull. 1992, 40, 846–850, respectively, all incorporated herein by reference. Barbituric acid, 1,5-diaminopentane, D- and L-N$^\alpha$-Boc-N$^\Sigma$-Cbz-Lysine, all the reagents and solvents are commercially available from Aldrich, Novabiochem, Fisher Scientific or Advanced ChemTech.
Scheme 1
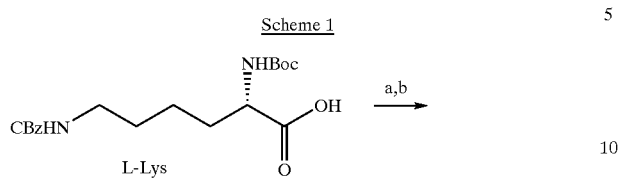
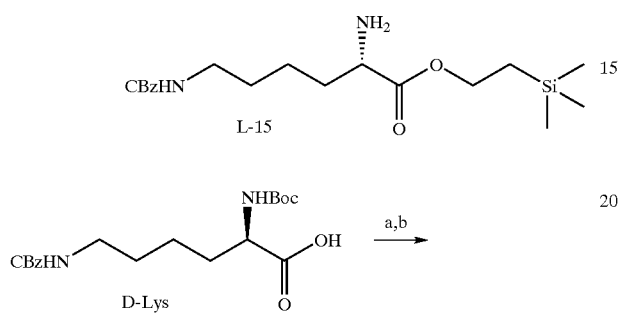
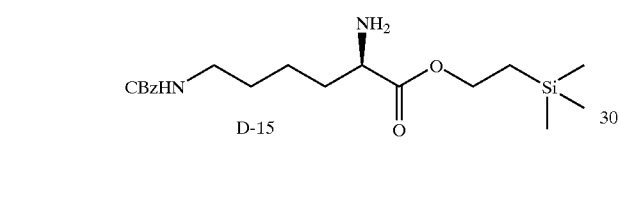
Scheme 2
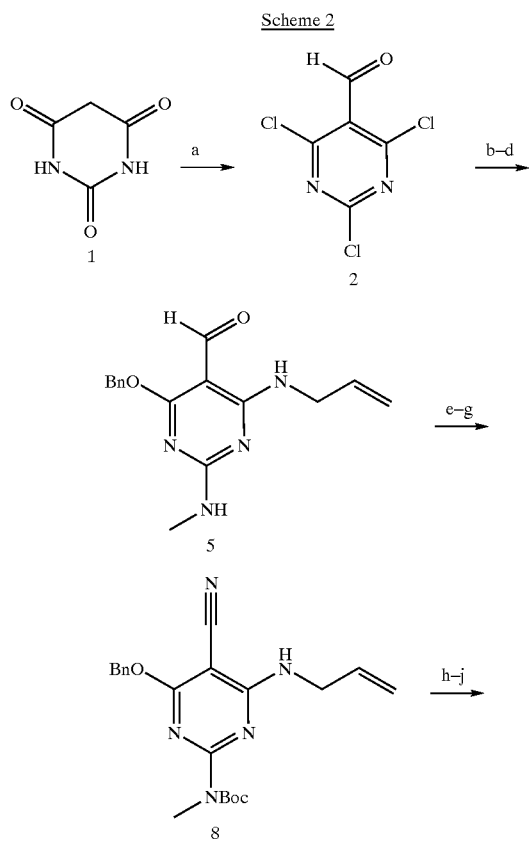
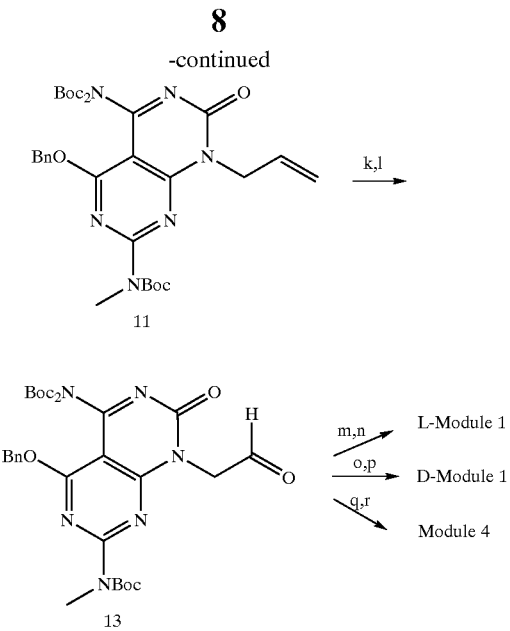
Scheme 3
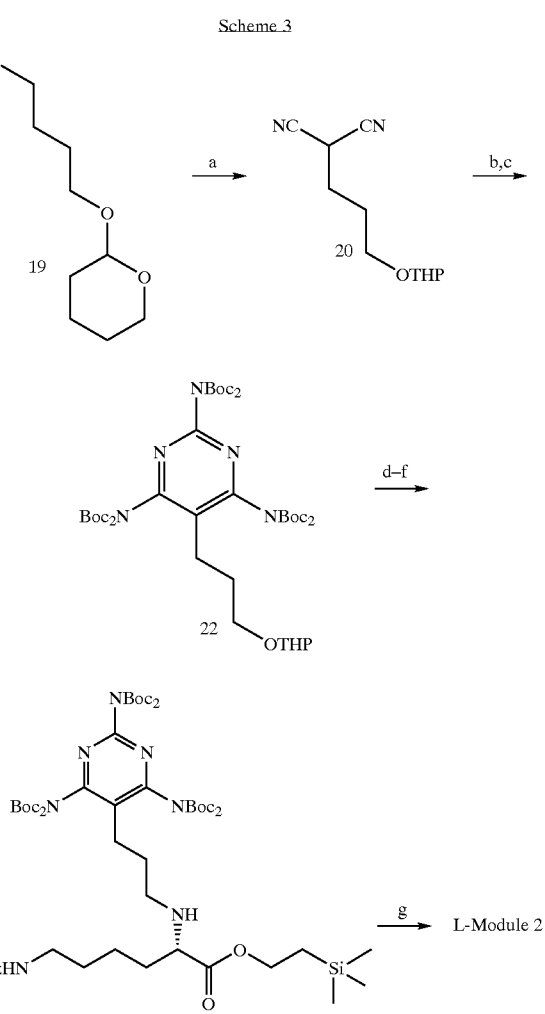

Scheme 4

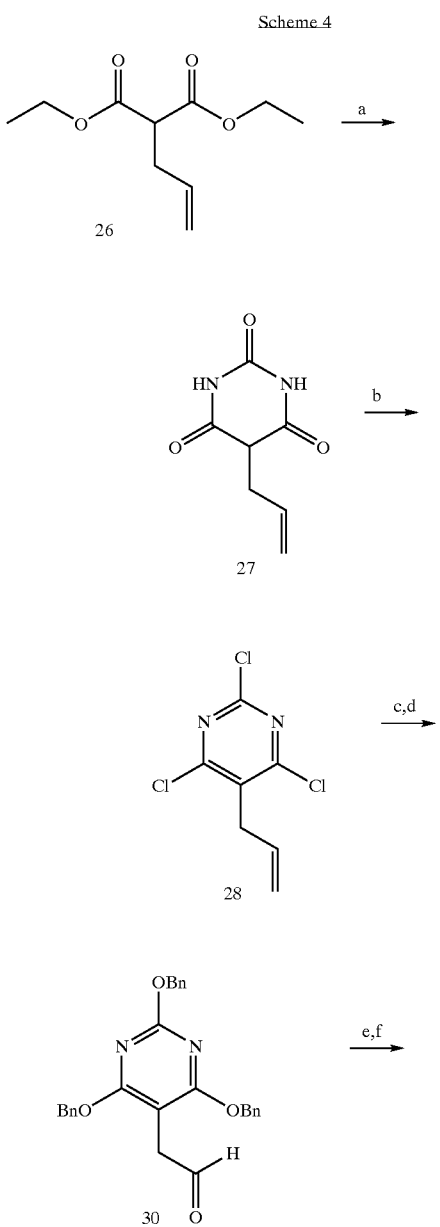

Scheme 1. (a) 2-Trimethylsilylethanol, DCC, DMAP, CH$_2$Cl$_2$, rt, 22 h, 95%. (b) 10% TFA:CH$_2$Cl$_2$, rt, 1.5 h, 95%.

Scheme 2. (a) 1, POCl$_3$, DMF, reflux, 15 h, 65%. (b) 2, Allylamine, CH$_2$Cl$_2$, −78°→−20° C., 7 h, 79%. (c) 3, CH$_3$NH$_2$, THF, 0°C.→rt, 7 h, 83%. (d) 4, benzylalcohol, NaH, THF, reflux, 22 h, 75%. (e) 5, (Boc)$_2$O, Et$_3$N, DMAP, THF, rt, 18 h, 88%. (f) 6, NH$_2$OH, MeOH, reflux, 3 h, 92%. (g) 7, TFAA, Et$_3$N, THF, 0° C.→reflux, 5 h, 79%. (h) 8, Cl(O=C)NCO, CH$_2$Cl$_2$, 0° C.→rt, 5 h, 97%. (i) 9, 7N—NH$_3$, MeOH, rt, 2 h, 59% from 8. (j) 10, (Boc)$_2$, Et$_3$N, DMAP, rt, 22 h, 89%. (k) 11, OsO$_4$, NMMO, Acetone:dH$_2$O (8:1), rt, 23 h, 98%. (l)12, NaIO$_4$, CH$_2$Cl$_2$:dH$_2$O (4:1), rt, 36 h, 86%. (m) L-15, 13, DIEA, 1,2-DCE, NaB(OAc)$_3$H, rt, 16 h, 72%. (n) L-16, Thioanisole:TFA (6:94), 60 h, 58%. (o) D-15, 13, DIEA, 1,2-DCE, NaB(OAc)$_3$H, rt, 16 h, 70%. (p) D-16, Thioanisole:TFA (6:94), rt, 86 h, 63%. (q) 5-tert-butoxycarbonylamino-1-aminopentane, 13, DIEA, 1,2-DCE, NaB(OAc)$_3$H, rt, 12 h, 55%.(r) 18, Thioanisole:TFA (6:94), rt, 86 h, 77%.

Scheme 3. (a) 19, malononitrile, NaH, DME, rt, 12 h, 88%. (b) 20, Na, EtOH, guanidinium hydrochloride, reflux, 5 h, 74%. (c) 21, (Boc)$_2$O, THF, DMAP, rt, 12 h, 45%. (d) 22, p-TsOH, MeOH, rt, 5 h, 98%. (e) 23, Dess-Martin reagent, CH$_2$Cl$_2$, rt, 2 h, 94%. (f) L-15, 24, DIEA, 1,2-DCE, NaB(OAc)$_3$H, rt, 12 h, 46%.(g) 25, Thioanisole:TFA (6:94), rt, 12 h, 82%.

Scheme 4. (a) 26, urea, Na, CH$_3$OH, reflux, 5 h, 67%. (b) 27, POCl$_3$, N,N-dimethylaniline, 70° C.→reflux, 4 h, 71%. (c) 28, benzylalcohol, NaH, THF, reflux, 12 h, 45%. (d) 29, NaIO$_4$, OsO$_4$, dioxane:dH$_2$O (4:1), rt, 12 h, 73%. (e) 30, L-15, DIEA, 1,2-DCE, NaB(OAc)$_3$H, rt, 12 h, 55%. (f) 31, Thioanisole:TFA (6:94), rt, 96 h, 65%.

As previously mentioned, the following is a more detailed discussion of the synthesis of the compounds. The abbreviations used are as follows: AcOH (acetic acid); Bn (benzyl) Boc (tert-butyloxycarbonyl); br (broaden); n-BuOH (1-butanol); Cbz (benzyloxycarbonyl); concd (concentrated); Cl-MS (chemical impact mass spectrometry); d (doublet); DCC (dicyclohexylcarbodiimide); 1,2-DCE (1,2-dichloroethane); DCU (dicyclohexylurea); dH$_2$O (deionized NanoPure water); DIEA (diisopropylethylamine); DMAP (4-N,N-dimethylaminopyridine); DME (1,2-dimethoxyethane) DMF (dimethylformamide); EA (ethylacetate); EI-MS (electron impact mass spectrometry); ESI-MS (electrospray ionization mass spectrometry); Et$_2$O (diethylether); EtOH (ethanol); Et$_3$N (triethylamine); FAB-MS (fast atom bombardment mass spectrometry); h (hour); KIPEG (potassium iodide and polyethyleneglycol matrix for FAB-MS); m (multiplet); min (minute); mp (melting point); NBA (4-nitrobenzylalcohol matrix for FAB-MS); NMMO (N-methylmorpholine N-oxide); NMR (nuclear magnetic resonance); p (pentuplet); PD-MS (plasma desorption mass spectrometry); p-TsOH (para-toluenesulfonic acid); q (quartet); R$_f$ (retention factor); rt (room temperature); s (singlet); sat (saturated); t-Bu (tert-butyl); TFA (trifluoroacetic acid); TFAA (trifluoroacetic anhydride); THF (tetrahydrofuran).

Melting points were recorded on a Thomas Hoover capillary melting point apparatus (Unimelt). $^1$H and $^{13}$C-NMR spectra were recorded on Varian NMR spectrometers (Gemini 200, Inova 300, Unity 500 or Unity Plus 600 MHz) with the solvent as internal reference. The NMR data is presented as follows: chemical shift, peak assignment, multiplicity, coupling constant, integration. The mass spectra were performed at the Mass Spectrometry Center of Purdue University. As discussed above compounds 2, 17, 19, and 26–28 were prepared according to previously reported procedures. Barbituric acid, 1,5-diaminopentane, D and L 6-benzyloxycarbonylamino-2-tert-butoxycarbonyl-aminohexanoic acid, all the reagents and solvents are commercially available from Aldrich, Novabiochem, Fisher Scientific or Advanced ChemTech. Reagent grade solvents were distilled under inert atmosphere (N$_2$) prior to use: CH$_2$Cl$_2$ was distilled over CaH$_2$, THF over Na/benzophenone and CH$_3$OH over Mg. All the reactions were performed under N$_2$ atmosphere.

For column chromatography, commercial solvents were used without purification. Chromatographic supports were silica flash Merck 60 (0.040–0.063 mm) or silica gel Merck 60 (0.063–0.2 mm) for gravity chromatography. Silica-coated TLC plates (Merck F 60$_{254}$) were used for monitoring reaction progress and visualizations were made under UV light or by chemical staining (KMnO$_4$/dH$_2$O, phosphomolybdic acid/EtOH, or ninhydrin/n-BuOH/AcOH).

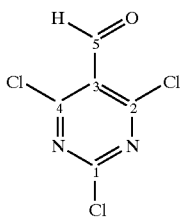

Synthesis of Compound 2

Barbituric acid 1 (structure not shown) (10 g, 78.1 mMol) was added to a stirred solution of $POCl_3$ (47 mL, 77.3 g, 504 mMol) and DMF (6 mL, 5.66 g, 77.5 mMol) at rt under $N_2$ atmosphere. The mixture was refluxed for 15 h then allowed to cool down to rt. Excess $POCl_3$ was removed under reduced pressure (high vacuum rotavap), and the resulting viscous material was carefully poured over crushed ice (250 g) while vigorously stirring. The resulting pale brown precipitate was then filtered and dried under high vacuum. The desired compound 2 ($C_5HCl_3N_2O$, 10.7 g, 65%) was obtained as yellow crystalline solid upon sublimation (120° C., 0.05 mm Hg). $R_f$=0.43 (10% EA/Hex). mp =130° C. $^1$H-NMR (300 MHz, $CDCl_3$) δ (ppm): 10.45 ($C_5H$, s,1H).

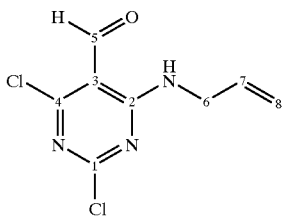

Synthesis of Compound 3

To a stirred solution of 2 (6.0 g, 28.4 mMol) in $CH_2Cl_2$ (50 mL), allylamine (3.34 g, 4.26 mL, 56.8 mmol) was slowly added at −78° C. under $N_2$ atmosphere. The resulting mixture was stirred at −78° C. for 2 h then allowed to warm to −20° C. over a period of 7 h. The reaction was then quenched with $dH_2O$ (10 mL) and extracted with $CH_2Cl_2$ (100 mL). The organic layer was washed with $dH_2O$ (2×50 mL) and brine (50 mL), then dried over anhydrous $Na_2SO_4$. After filtration and evaporation of the solvent (rotavap) the crude product was purified by gravity silica gel chromatography (0 to 2% EA/Hex). The desired compound 3 was obtained as a colorless liquid ($C_8H_7Cl_2N_3O$, 5.29 g, 79%). $R_f$=0.33 (10% EA/Hex). $^1$H-NMR (200 MHz, $CDCl_3$) δ (ppm): 10.25 ($C_5H$, s, 1H), 9.32 ($NHC_6$, br, s, 1H), 5.94–5.79 ($C_7H$, m, 1H), 5.25–5.12 ($C_8H$, m, 2H), 4.20–4.13 ($C_6H$, m, 2H). $^{13}$C-NMR (50 MHz, $CDCl_3$) δ (ppm): 190.9 ($C_5$), 166.46 ($C_2$),163.14 ($C_1$), 162.00 ($C_4$), 132.73 ($C_7$), 117.99 ($C_8$), 107.15 ($C_3$), 44.01($C_6$). Positive ESI-MS: Expected mass for (M+H$^+$)/z, 232.00. Observed, 232.1 ((M+H$^+$)/z, 93%).

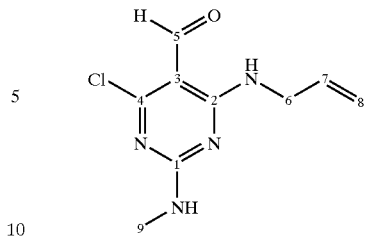

Synthesis of Compound 4

To a stirred solution of 3 (9.1 g, 39.2 mMol) in THF (100 mL), methylamine (2 M solution in THF, 39.2 mL, 78.4 mMol,) was added at 0° C. under $N_2$ atmosphere. The reaction mixture was stirred at 0° C. for 1 h then at rt for 6 h. The reaction was quenched with sat aqueous $NH_4Cl$ (10 mL) and the solvent was removed under reduced pressure (rotovap). The desired product 4 ($C_9H_{11}ClN_4O$, 7.36 g, 83%) was obtained as a crystalline white solid after gravity silica gel chromatography. $R_f$=0.22 ($SiO_2$, 10% EA/Hex). mp =156° C. $^1$H-NMR (200 MHz, $CDCl_3$) δ (ppm): 10.03 ($C_5H$, s, 1H), 9.37 ($NHC_6$, br, s, 1H), 6.92 ($NHC_9$, br, s, 1H), 5.95–5.86 ($C_7H$, m, 1H), 5.28–5.14 ($C_8H$, m, 2H), 4.18 ($C_6H$, t, J 5.4 Hz, 2H), 3.01 ($C_9H$, d, J=4.76 Hz, 3H). $^{13}$C-NMR (50 MHz, $CDCl_3$) δ (ppm): 188.83 ($C_5$), 165.77 ($C_3$), 162.65 ($C_4$), 161.94 ($C_2$), 134.12 ($C_8$), 116.97 ($C_7$), 102.04 ($C_1$), 43.44($C_6$), 28.71($C_9$). EI-MS: Expected mass for (M$^+$)/z, 226.06 Observed, 226 ((M$^+$)/z, 67%), 211 ((M$^+$)/z-CH$_3$, 100%). High resolution EI-MS: Expected mass for (M$^+$)/z, 226.0621 Observed, 226.0624.

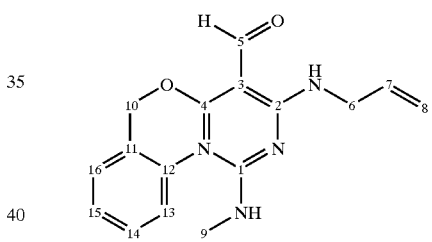

Synthesis of Compound 5

Benzyl alcohol (6.68 g, 6.39 mL, 61.8 mMol) was added to a stirred suspension of 95% NaH (1.79 g, 70.8 mMol) in THF (10 mL) at rt under $N_2$ atmosphere. After 15 min, the solution was cooled to 0° C. then a solution of compound 4 (7.0 g, 30.9 mMol) in THF (40 mL) was added. The mixture was allowed to warm to rt then it was refluxed for 22 h. The mixture was then cooled to 0° C. and carefully quenched with sat $NH_4Cl$ (5 mL). The solvent was removed under reduced pressure (rotavap), and the residual solid was dissolved in $Et_2O$, washed with $dH_2O$ (100 mL) and brine (50 mL) and dried over anhydrous $Na_2SO_4$. Filtration, evaporation of the solvent under reduced pressure (rotavap) followed by gravity silica gel chromatography (0 to 5% EA/Hex) yielded 5 as a white solid ($C_{16}H_{18}N_4O_2$, 7.0 g, 75%). $R_f$=0.51 (30% EA/Hex). mp=56° C. $^1$H—NMR (200 MHz, $CDCl_3$)δ (ppm): 10.32 ($C_5H$, s, 1H), 9.42 ($NHC_6$, br, s, 1H, major isomer), 9.25 ($NHC_6$, br, s, 1H, minor isomer), 7.49–7.37 ($C_{12}H$—$C_{16}H$, m, 5H), 6.03–5.84 ($C_7H$, br, m, 1H), 5.46–5.10 ($C_8H$, $C_{10}H$, m, 4 H), 4.19 ($C_6H$, br, s,2H, major isomer), 4.06 ($C_6H$, br, s, 2H, minor isomer), 2.98 ($C_9H$, d, J=8.5 Hz, 3H). $^{13}$C-NMR (50 MHz, $CDCl_3$) δ (ppm): 186.42 ($C_5$), 163.86 ($C_3$), 163.37 ($C_4$), 141.82 ($C_2$), 137.09 ($C_{11}$), 134.79 ($C_8$), 129.03, 128.93, 127.43 ($C_{12}$–$C_{16}$), 116.43 ($C_7$), 93.92 ($C_1$), 68.06 ($C_{10}$), 43.32 ($C_6$), 28.68 ($C_9$). EI-MS: Expected mass for ($M^+$)/z, 298.14. Observed, 298 (($M^+$)/z, 15%), 283 (($M^+$)/z-$CH_3$, 2.1%), 207 (($M^+$)/z-$C_7H_7$, 27%), 91 (($C_7H_7$)$^+$, 100%). High resolution EI-MS: Expected mass for ($M^+$)/z, 298.1430. Observed, 298.1424.

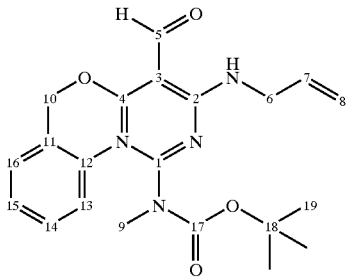

Synthesis of Compound 6

To a stirred solution of compound 5 (5.0 g, 16.8 mMol), DMAP (1.0 g, 8.35 mMol) and THF (50 mL), $Et_3N$ (5.1 g, 7.0 mL, 50.3 mMol) was added at rt under $N_2$ atmosphere. After stirring for 5 min, $Boc_2O$ (4.39 g, 20.1 mMol) was added, and the mixture was stirred at rt for 18 h. The reaction was quenched with $dH_2O$ (10 mL) followed by removal of the solvent under reduced pressure (rotovap). The residual solid was dissolved in EA (300 mL) and washed with 10% aqueous citric acid (50 mL), $dH_2O$ (2×50 mL), 5% aqueous $NaHCO_3$ (50 mL) and brine (50 mL). After drying the organic layer over anhydrous $Na_2SO_4$, filtration and removal of the solvent under reduced pressure (rotovap), the residue was purified by gravity silica gel chromatography (0 to 5% EA/Hex). The desired compound 6 ($C_{21}H_{26}N_4O_4$, 5.86 g, 88%) was obtained as a white crystalline solid. $R_f$=0.38 (10% EA/Hex). mp=54° C. $^1$H-NMR (300 MHz, $CDCl_3$) δ (ppm): 10.18 ($C_5H$, s, 1H), 9.26 ($NHC_6$, br, t, J=5.7 Hz, 1H), 7.49–7.36 ($C_{12}H$—$C_{16}H$, br, m, 5H), 6.01–5.90 ($C_7H$, m, 1H), 5.53 ($C_{10}H$, s, 2H), 5.31–5.14 ($C_8H$, br, m, 2H), 4.23 ($C_6H$, t, 2H, J=4.8 Hz), 3.43 ($C_9H$, s, 3H), 1.59 ($C_{19}H$, s, 9H). $^{13}$C-NMR (50 MHz, $CDCl_3$) δ (ppm): 188.09 ($C_5$), 171.89 ($C_{17}$), 163.16 ($C_1$), 162.30 ($C_2$), 154.25 ($C_4$), 136.79 ($C_{11}$), 134.57 ($C_7$), 129.03 ($C_{12}$–$C_{16}$), 128.68 ($C_{12}$–$C_{16}$), 128.54 ($C_{12}$–$C_{16}$), 116.70 ($C_8$), 94.75 ($C_3$), 82.39 ($C_{18}$), 68.74 ($C_{10}$), 43.48 ($C_6$), 35.15 ($C_9$), 28.69 ($C_{19}$). Cl-MS: Expected mass for ($M+H^+$)/z, 399.20. Observed, 399 (($M+H^+$)/z, 100%), 299 (($M+H^+$)/z-Boc, 7.1%). High resolution EI-MS: Expected for ($M^+$)/z, 398.1954. Observed, 398.1943.

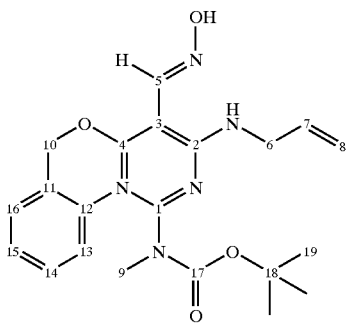

Synthesis of Compound 7

To a stirred solution of 6 (4.2 g, 10.6 mMol) in anhydrous methanol (100 mL) $KHCO_3$ (4.23 g, 42.2 mMol) and hydroxylamine hydrochloride (1.47 g, 21.1 mMol) were added at rt under $N_2$ atmosphere. The resulting slurry was refluxed for 3 h then cooled to rt and quenched with $dH_2O$ (10 mL). The solvent was removed (rotovap) and the residual solid was dissolved in EA (200 mL), washed with $dH_2O$ (50 mL) and brine (25 mL). The organic layer was dried over anhydrous $Na_2SO_4$, filtered, and evaporated to dryness (rotavap) to yield compound 7 ($C_{21}H_{27}NO_4$, 4 g, 92%). This material was used in the next step without further purification. $R_f$=0.50 (30% EA/Hex). $^1$H-NMR (200 MHz, $CDCl_3$) δ (ppm): 8.58 ($C_5H$, s, 1H), 8.05 ($NHC_6$, t, J=6.5 Hz, 1H), 7.60 (NOH, br, s, 1H) 7.46–7.34 ($C_{12}H$—$C_{16}H$, m, 5H), 6.06–5.80 ($C_7H$, m, 1H), 5.44 ($C_{10}H$, s, 2H), 528–5.10 ($C_8H$, m, 2H), 4.25–4.18 ($C_6H$, m, 2H), 3.41 ($C_9H$, s, 3H), 1.89 ($C_{19}H$, s, 9H). $^{13}$C-NMR (50 MHz, $CDCl_3$) δ (ppm): 167.63 ($C_5$), 161.16 ($C_4$), 159.53 ($C_2$), 155.03 ($C_{17}$), 146.42 ($C_1$), 137.25 ($C_{11}$), 135.30 ($C_7$), 128.95, 128.74 ($C_{12}$–$C_{16}$), 116.07 ($C_8$), 88.54 ($C_3$), 81.96 ($C_{18}$), 68.63 ($C_{10}$), 43.85 ($C_6$), 35.34 ($C_9$), 28.84 ($C_{19}$). Cl-MS: Expected mass for ($M+H^+$)/z, 414.20 Observed, 414 (($M+H^+$)/z, 100%), 396 (($M+H^+$)/z-$H_2O$, 18.3%), 314 (($M+H^+$)/z-Boc, 18.3%). High resolution EI-MS: Expected for ($M^+$)/z, 413.2063. Observed, 413.2050.

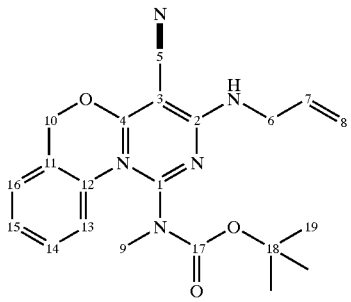

Synthesis of Compound 8

Compound 7 (4.0 g, 9.66 mMol), $Et_3N$ (4.03 mL, 2.93 g, 29.0 mMol) and THF (50 mL) were cooled to 0° C. then TFA (2.0 mL, 3.04 g, 14.5 mMol) was slowly added. After stirring for 15 min, the mixture was allowed to warm to rt then it was refluxed for 5 h. After cooling down to rt the reaction was quenched with $dH_2O$ (10 mL) and the solvent was removed under reduced pressure (rotovap). The residual solid was dissolved in EA (300 mL), washed with $dH_2O$ (2×50 mL), 10% aqueous citric acid (25 mL), $dH_2O$ (50 mL), 5% aqueous $NaHCO_3$ (50 mL) and brine (50 mL). The organic layer was dried over anhydrous $Na_2SO_4$, filtered, and evaporated to dryness under reduced pressure (rotavap). Compound 8 was obtained as a white solid ($C_{21}H_{25}N_5O_3$, 3.3 g, 79% from 6) after gravity silica gel chromatography (3% EA/Hex). $R_f$=0.64 (30% EA/Hex). mp=68° C. $^1$H-NMR (300 MHz, $CDCl_3$) δ (ppm): 7.49–7.35 ($C_{12}H$-$C_{16}H$, m, 5H), 5.91–5.83 ($C_7H$, m, 1H), 5.78 ($NHC_6$, t, J=5.6 Hz, 1H), 5.51 ($C_{10}H$, s, 2H), 5.27 ($C_8H$, d, J=17.1 Hz, 1H), 5.19 ($C_8H$, d, J=10.1 Hz, 1H), 4.18 ($C_6H$, t, J=5.7 Hz, 2H), 3.40 ($C_9H$, s, 3H), 1.58 ($C_{19}H$, S, 9H). $^{13}$C-NMR (75 MHz, $CDCl_3$) δ (ppm): 170.62 ($C_{17}$), 164.31 ($C_1$), 161.05 ($C_2$), 153.80 ($C_4$), 136.26 ($C_{11}$), 134.14 ($C_7$), 128.76 ($C_{12}$–$C_{16}$), 128.44 ($C_{12}$–$C_{16}$), 128.25 ($C_{12}$–$C_{16}$), 117.20 ($C_8$), 115.05 ($C_5$), 82.27 ($C_{18}$), 69.06 ($C_{10}$), 68.83 ($C_3$), 43.90 ($C_6$), 34.94($C_9$), 28.47 ($C_{19}$). Cl-MS: Expected mass for ($M+H^+$)/z, 396.20. Observed, 396 (($M+H^+$)/z, 100%), 296 (($M+H^+$)/z-Boc, 32%). High resolution EI-MS: Expected for ($M^+$)/z, 395.1957. Observed, 395.1961.

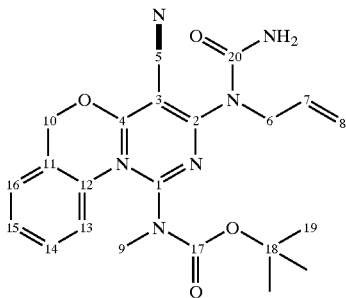

Synthesis of Compound 9

To a solution of compound 8 (15.2 g, 38.4 mMol) in $CH_2Cl_2$ (300 mL), N-chlorocarbonylisocyanate (Gorbatenko, Tetrahedron 1993, 49, 3227–3257 incorporated herein by reference) (8.09 g, 6.2 mL, 76.7 mMol) was added dropwise at 0° C. over a period of 15 min under $N_2$ atmosphere. After stirring for 2 h at 0° C., the mixture was allowed to warm to rt and was stirred for an additional 3 h. The reaction mixture was cooled to 0° C. and carefully quenched with $dH_2O$ (10 mL, exothermic reaction!) followed by 5% aqueous $NaHCO_3$ (10 mL). The product was extracted with chloroform (1500 mL) and the resulting organic layer was washed with $dH_2O$ (2×100 mL), brine (100 mL) and dried over anhydrous $Na_2SO_4$. Filtration and evaporation of the organic solvents under reduced pressure (rotavap) yielded 9 ($C_{22}H_{26}N_6O_4$, 16.4 g, 97%) as a viscous liquid, which was used in the next step without further purification. A small sample of this compound was purified by gravity silica gel chromatography (30% EA/Hex) to yield 9 as an analytically pure white solid. $R_f$=0.16 (30% EA/Hex). mp=98° C. $^1$H-NMR (200 MHz, $CDCl_3$) δ (ppm): 7.46 ($C_{12}H$-$C_{16}H$, br, m, 5H), 5.94–5.75 ($C_7H$, m, 1H), 5.51 ($C_{10}H$, s, 2H), 5.18 ($C_8H$, t, J=21.2 Hz, 2H), 4.92 ($C_6H$, d, J=5.4 Hz, 2H), 3.41 ($C_9H$, s, 3H), 1.54 ($C_{19}H$, s, 9H). $^{13}$C-NMR (50 MHz, $CDCl_3$) δ (ppm): 172.54 ($C_{17}$), 163.51 ($C_1$), 159.08 ($C_2$), 155.86 ($C_4$), 152.95 ($C_{20}$), 135.70 ($C_{11}$), 133.82 ($C_7$), 129.14, 128.93, 128.21 ($C_{12}$–$C_{16}$), 117.34 ($C_8$), 114.44 ($C_5$), 83.90 ($C_{18}$), 70.18 ($C_{10}$), 48.51 ($C_6$), 34.99 ($C_9$), 28.51 ($C_{19}$). Cl-MS: Expected mass for (M+H$^+$)/z, 439.20. Observed, 439 ((M+H$^+$)/z, 2.8%), 396 ((M+H$^+$)/z —$CONH_2$, 100%), 296 ((M+H$^+$)/z-(Boc+$CONH_2$), 39%). High resolution EI-MS: Expected mass for (M$^+$)/z, 438.2016. Observed, 438.2027.

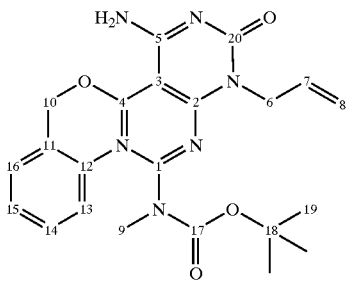

Synthesis of Compound 10

Compound 9 (16.4 g, 37.3 mmol) was stirred in 7 N $NH_3$ in $CH_3OH$ (450 mL) under $N_2$ atmosphere at rt for 2 h. Excess $CH_3OH$ was removed under reduced pressure (rotovap) and the desired compound 10 was obtained as a white solid ($C_{22}H_{26}N_6O_4$, 9.94 g, 59% from 8) after gravity silica gel chromatography (50 to 100% Hex/EA, then 0 to 3% $CH_3OH/CHCl_3$). $R_f$=0.26 (EA). mp=192° C. $^1$H-NMR (300 MHz, $CDCl_3$) δ (ppm): 8.00 ($NHC_5$, br, s, 1H), 7.51–7.41 ($C_{12}H$—$C_{16}H$, m, 5H), 7.15 ($NHC_5$, S, 1H), 6.02–5.91 ($C_7H$, br, m, 1H), 5.66 ($C_{10}H$, s, 2H), 5.27 ($C_8H$, d, J=17.2 Hz, 1H), 5.18 ($C_8H$, d, J=10.2 Hz, 1H), 4.87 ($C_6H$, d, J=5.6 Hz, 2H), 3.47 ($C_9H$, s, 3H), 1.61 ($C_{19}H$, s, 9H) $^{13}$C-NMR (50 MHz, $CDCl_3$) δ (ppm): 167.04 ($C_{17}$), 161.72 ($C_1$), 161.09 ($C_2$), 160.83 ($C_5$), 156.37 ($C_4$), 153.53 ($C_{20}$), 135.58 ($C_{11}$), 132.99 ($C_7$), 129.27, 129.07 ($C_{12}$–$C_{16}$), 117.80 ($C_8$), 86.65 ($C_3$), 82.97 ($C_{18}$), 70.31 ($C_{10}$), 45.01 ($C_6$), 35.26 ($C_9$), 28.64 ($C_{19}$). Cl-MS: Expected mass for (M+H$^+$)/z, 439.20. Observed, 439 ((M+H$^+$)/z, 100%), 339 ((M+H$^+$)/z-Boc, 29%). Positive high resolution Cl-MS: Expected mass for (M+H$^+$)/z, 439.2094. Observed, 439.2096.

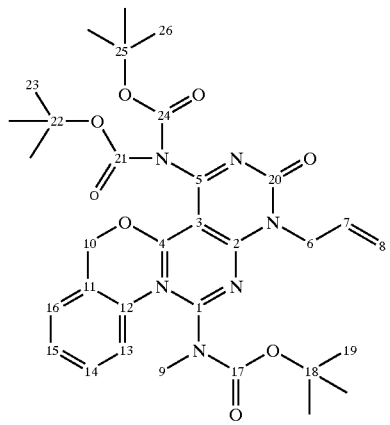

Synthesis of Compound 11

To a solution of compound 10 (2.5 g, 5.69 mMol), DMAP (0.7 g, 5.69 mmol) and $Et_3N$ (4.8 mL, 3.5 g, 34.2 mMol) in THF (50 mL), $Boc_2O$ (3.72 g, 17.1 mMol) was added under $N_2$ atmosphere. After stirring at rt for 22 h, the reaction was quenched with $dH_2O$ (10 mL) and the solvent was removed under reduced pressure (rotovap). The residual solid was dissolved in EA (300 mL), washed with $dH_2O$ (100 mL), 10% aqueous citric acid (50 mL), $dH_2O$ (2×50 mL), 5% aqueous $NaHCO_3$ (50 mL) and brine (50 mL), then dried over anhydrous $Na_2SO_4$. After filtration and removal of the solvent under reduced pressure (rotavap) the residual solid was purified by gravity silica gel chromatography (5 to 20% EA/Hex) to yield compound 11 ($C_{32}H_{42}N_6O_8$, 3.25 g, 89%) as a white foam. $R_f$=0.66 (50% EA/Hex). mp=78° C. $^1$H-NMR (200 MHz, $CDCl_3$) δ (ppm): 7.48–7.44 ($C_{12}H$–$C_{16}H$, m, 5H), 6.07–5.87 ($C_7H$, m, 1H), 5.58 ($C_{10}H$, s, 2H), 5.24 ($C_8H$, t, J=12.4 Hz, 2H), 4.94 ($C_6H$, d, J=9.2 Hz, 2H), 3.46 ($C_9H$ s, 3H), 1.59 ($C_{19}H$, s, 9H), 1.35 ($C_{23}H$ and $C_{26}H$, s, 18H). $^{13}$C-NMR (50 MHz, $CDCl_3$) δ (ppm): 165.96 ($C_{17}$), 161.37 ($C_{24}$ or $C_{22}$), 161.06 ($C_{22}$ or $C_{24}$), 160.67 ($C_1$), 155.60 ($C_4$), 152.88 ($C_{20}$), 149.41 ($C_2$, $C_5$), 135.19 ($C_{11}$), 131.48 ($C_7$), 128.85, 128.72 ($C_{12}$–$C_{16}$), 118.26 ($C_8$), 93.08 ($C_3$), 83.83 ($C_{23}$, $C_{26}$), 83.23 ($C_{18}$), 70.35 ($C_{10}$), 45.49 ($C_6$) 35.16 ($C_9$), 28.35 ($C_{19}$), 28.05 ($C_{23}$, $C_{26}$). EI-MS: Expected mass for (M+H$^+$)/z, 638.31. Observed 639.8 ((M+H$^+$)/z, 89%). High resolution EI-MS: Expected for (M$^+$)/z, 638.3064. Observed, 638.3057.

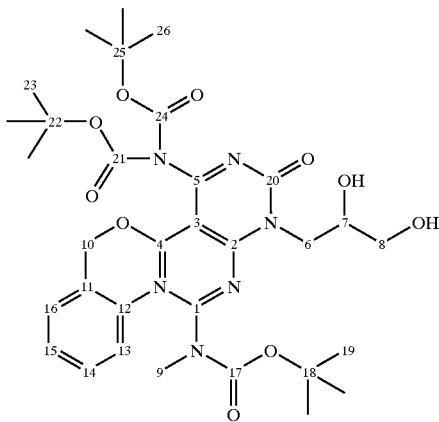

Synthesis of Compound 12

To a stirred solution of compound 11 (3.2 g, 5.01 mMol) in acetone:$dH_2O$ (8:1, 90 mL) was added 50% aqueous NMMO (1.17 g, 2.4 mL, 10.0 mMol) at rt. After stirring for 5 min, $OsO_4$ (0.1 M solution in t-BuOH, 2.5 mL, 0.25 mMol) was added dropwise over a period of 5 min. The resulting brown solution was stirred at rt for 23 h then quenched with aqueous sodium sulfite until all the excess $OsO_4$ was destroyed (brown solution turns colorless). Diol 12 was extracted in $CHCl_3$ (250 mL) and washed with $dH_2O$ (2×10 mL) and brine (25 mL). The organic layer was dried over anhydrous $Na_2SO_4$, filtered, and evaporated to dryness under reduced pressure (rotavap). Crystallization from EA yielded compound 12 as a white solid ($C_{32}H_{44}N_6O_{10}$, 3.31 g, 98%). $R_f$=0.15 (50% EA/Hex). mp=136° C. $^1$H-NMR (300 MHz, $CDCl_3$) δ (ppm): 7.46 ($C_{12}H$—$C_{16}H$, br, m, 5H), 5.61 ($C_{10}H$, s, 2H), 4.63 ($C_6H$, d, J=4.5 Hz, 2H), 4.18 ($C_7H$, m, 1H), 4.09 ($C_7OH$, d, J=5.6 Hz, 1 H), 3.60 ($C_8H$, m, 2H), 3.51 ($C_9H$, s, 3H), 3.28 ($C_8OH$, t, J=7.2 Hz), 1.62 ($C_{19}H$, s, 9H,), 1.39 ($C_{23}H$, $C_{26}H$, s, 18H). $^{13}$C-NMR (50 MHz, $CDCl_3$) δ (ppm): 166.33 ($C_{17}$), 162.24 ($C_1$), 161.25 ($C_{21}$), 160.00 ($C_{24}$), 157.36 ($C_4$), 152.81 ($C_{20}$), 149.71 ($C_2$), 149.63 ($C_5$), 135.15 ($C_{11}$), 129.14, 128.51 ($C_{12}$–$C_{16}$), 93.76 ($C_3$), 84.46 ($C_{22}$, $C_{25}$), 84.34 ($C_{18}$), 71.18 ($C_7$), 70.77 ($C_8$), 63.79 ($C_{10}$), 45.90 ($C_6$), 35.21 ($C_9$), 28.52 ($C_{19}$), 28.29 ($C_{26}$, $C_{23}$). Cl-MS: Expected mass for $(M+H^+)$/z, 673.31. Observed 673.8 $((M+H^+)$/z, 100%), 573.8 $((M+H^+)$/z-Boc, 23%). EI-MS: Expected mass for $(M^+)$/z, 672.31. Observed 711 $((M+K^+)$/z, 11%), 672.2 $((M^+)$/z, 33%), 373 $((M+H^+)$/z-3Boc, 93%). High resolution EI-MS: Expected mass for $(M^+)$/z, 672.3119. Observed, 672.3131.

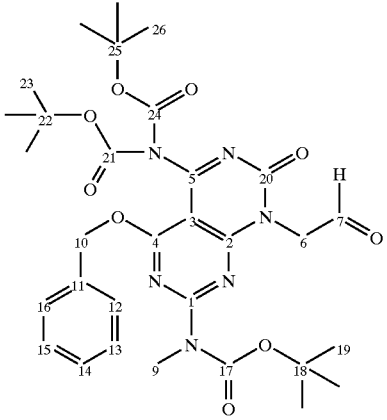

Synthesis of Compound 13

A solution of compound 12 (12.0 g, 17.8 mMol) in $CH_2Cl_2$/$dH_2O$ (4:1, 250 mL) and sodium periodate (7.63 g, 35.7 mMol) was stirred at rt for 36 h. The mixture was then filtered through a pad of celite and washed with $CH_2Cl_2$ (2×200 mL). Separation and evaporation of the organic layer under reduced pressure (rotavap) followed by gravity silica gel chromatography (5 to 30% EA/Hex) yielded compound 13 ($C_{31}H_{40}N_6O_9$, 9.82 g, 86%) as a white foam. $R_f$=0.48 (30% EA/Hex). mp=152° C. $^1$H-NMR (300 MHz, $CDCl_3$) δ (ppm): 9.58 ($C_7H$, d, J=1.2 Hz, 1H), 7.39–7.29 ($C_{12}H$—$C_{16}H$, br, m, 5H), 5.53 ($C_{10}H$, s, 5.09 ($C_6H$, s, 2H), 3.34 ($C_9H$, s, 3H), 1.49 ($C_{19}H$, s, 9H), 1.27 ($C_{23}H$, $C_{26}H$, s, 2H), 18H). $^{13}$C-NMR (75 MHz, $CDCl_3$) δ (ppm): 193.96 ($C_7$), 165.82 ($C_{17}$), 161.24 ($C_{21}$), 161.16 ($C_{24}$), 160.88 ($C_1$), 155.57 ($C_4$), 152.51 ($C_{20}$), 149.18 ($C_2$, $C_5$), 134.93 ($C_{11}$), 128.83, 128.79, 128.62 ($C_{12}$–$C_{16}$), 92.99 ($C_3$), 84.04 ($C_{22}$, $C_{25}$), 83.39 ($C_{18}$), 70.42 ($C_{10}$), 52.20 ($C_6$), 35.05 ($C_9$), 28.23 ($C_{19}$), 27.94 ($C_{26}$, $C_{23}$). PD-MS: Expected mass for $(M+H^+)$/z, 641.29. Observed, 678.7 $((M+H^+)$/z+$K^+$), 641.7 $((M+H^+)$/z), 613.0 $((M+H^+)$/z-CO). High resolution Cl-MS: Expected for $(M+H^+)$/z, 641.2935. Observed, 641.2945.

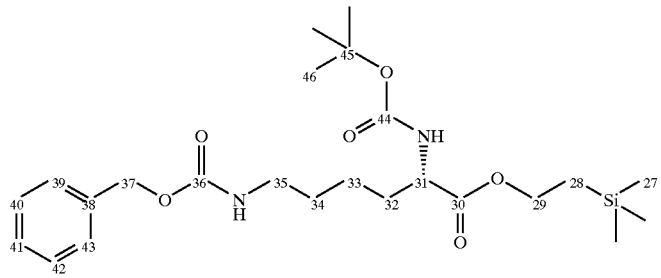

Synthesis of Compound L-14

To a stirred solution of 6-benzyloxycarbonylamino-2-tert-butoxycarbonyl-L-amino-hexanoic acid (5.0 g, 13.4 mMol), DMAP (0.161 g, 1.32 mMol) and 2-trimethylsilylethanol (1.55 g, 13.1 mMol) in $CH_2Cl_2$ (50 mL), DCC (2.98 g, 14.5 mMol) was added at 0° C. under $N_2$ atmosphere. After 15 min at 0° C., the mixture was stirred at rt for an additional 22 h. The solution was filtered to remove the DCU formed and concentrated under reduced pressure (rotavap). L-14 was obtained as a colorless viscous liquid ($C_{24}H_{40}N_2O_6Si$, 6.0 g, 95%) after gravity silica gel chromatography (0 to 5% EA/Hex). $R_f$=0.57 (30% EA/Hex). $^1$H-NMR (200 MHz, CDCl$_3$) δ (ppm): 7.39 ($C_{39}$H—$C_{43}$H, s, 5H), 5.14 ($C_{37}$H, s, 2H), 4.88 ($C_{31}$H, br, s, 1H), 4.23 ($C_{29}$H, t, J=9.0 Hz, 2H), 3.18 ($C_{35}$H, q, J=9.0 Hz, 1H), 1.91–1.11 ($C_{32}$H, $C_{33}$H, $C_{34}$H, br, m, 6H), 1.46 ($C_{46}$H s, 9H), 1.00 ($C_{28}$H, t, J=9.0 Hz, 2H), 0.06 ($C_{27}$H, s, 9H). $^{13}$C-NMR (50 MHz, CDCl$_3$) δ (ppm): 172.70 ($C_{30}$), 156.33 ($C_{44}$), 155.31 ($C_{36}$), 136.46 ($C_{38}$), 128.26, 127.87, 127.82 ($C_{39}$–$C_{43}$), 79.50 ($C_{45}$), 66.31 ($C_{37}$), 63.43 ($C_{29}$), 53.12 ($C_{31}$), 40.41 ($C_{35}$), 32.11 ($C_{32}$), 29.15 ($_{33}$), 28.12 ($C_{46}$), 22.22 ($C_{34}$), 17.15 ($C_{28}$), -1.71 ($C_{27}$). Positive ESI-MS: Expected mass for (M+H$^+$)/z, 481.27. Observed, 480.6 ((M+H$^+$)/z, 91%), 503.1 ((M+Na$^+$)/z, 100%). High resolution EI-MS: Expected for (M+H$^+$)/z, 480.2656. Observed, 480.2662.

($C_{45}$), 66.27 ($C_{37}$), 63.40 ($C_{29}$), 53.41 ($C_{31}$), 40.44 ($C_{35}$), 31.95 ($C_{32}$), 29.28 ($C_{33}$), 28.27 ($C_{46}$), 22.43 ($C_{34}$), 17.25 ($C_{28}$), -1.56 ($C_{27}$). Cl-MS: Expected mass for (M+H$^+$)/z, 481.27. Observed, 481 ((M+H$^+$)/z, 10%), 381((M+H$^+$)/z-Boc, 100%).

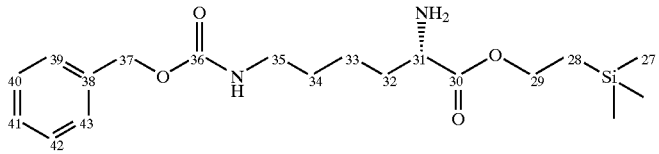

Synthesis of Compound L-15

A solution of compound L-14 (1.4 g, 2.91 mMol) in 10% TFA/CH$_2$Cl$_2$ (50 mL) was stirred at rt under N$_2$ atmosphere for 1.5 h then the excess TFA and solvent was removed under reduced pressure (rotavap). The resulting viscous material was dissolved in CH$_2$Cl$_2$ (50 mL) and concentrated once again under reduced pressure (rotavap) to yield the TFA salt of compound L-15 ($C_{19}H_{32}N_2O_4Si$—CF$_3$CO$_2$H, 1.35 g, 95%) as a colorless foam. This compound was used in the next step without further purification. $R_f$=0.5 (10% CH$_3$OH/CHCl$_3$). $^1$H-NMR (200 MHz, CDCl$_3$ with a drop of CH$_3$OD) δ (ppm): 7.30 ($C_{39}$H—$C_{43}$H, m, 5H), 5.03 ($C_{37}$H, s, 2H), 4.26 ($C_{29}$H, t, J=9.0 Hz, 2H), 3.92 ($C_{31}$H, br, t, J=3.0 Hz, 1H), 3.12 ($C_{35}$H, br, s, 2H), 1.89 ($C_{32}$H, br, s, 2H), 1.46 ($C_{33}$H, $C_{34}$H, br, s, 4H), 1.01 ($C_{28}$H, t, J=9.2 Hz, 2H), 0.01 ($C_{27}$H, s, 9H). $^1$H-NMR (300 MHz, CDCl$_3$ with a drop of TFA) δ (ppm): 8.60–8.20 (TFA, br, s, 6H), 7.31 ($C_{39}$H—$C_{43}$H, s, 5H), 5.06 ($C_{37}$H, s, 2H), 4.32–4.26 ($C_{29}$H, m, 2H), 3.98 ($C_{31}$H, br, s, 1H), 3.15 ($C_{35}$H, br, s, 2H), 1.95 ($C_{32}$H, br, s, 2H), 1.80–1.20 ($C_{33}$H, $C_{34}$H, m, 4H), 1.05–1.00 ($C_{28}$H, m, 2H), 0.04 ($C_{27}$H, s, 9H). $^{13}$C-NMR (75 MHz, CDCl$_3$) δ (ppm): 169.79 ($C_{30}$), 157.87 ($C_{36}$), 136.45 ($C_{38}$), 128.69, 128.33, 127.90 ($C_{39}$–$C_{43}$), 67.19 ($C_{37}$), 65.87 ($C_{29}$), 53.44 ($C_{31}$), 40.36 ($C_{35}$), 29.88 ($C_{32}$), 29.13 ($C_{34}$), 21.81 ($C_{33}$), 17.37 ($C_{28}$), -1.88 ($C_{27}$). Cl-MS: Expected mass for (M+H$^+$)/z, 381.21. Observed, 381.10 ((M+H$^+$)/z, 26%). High resolution ESI-MS: Expected mass for (M+H$^+$)/z, 381.2210. Observed, 381.2214.

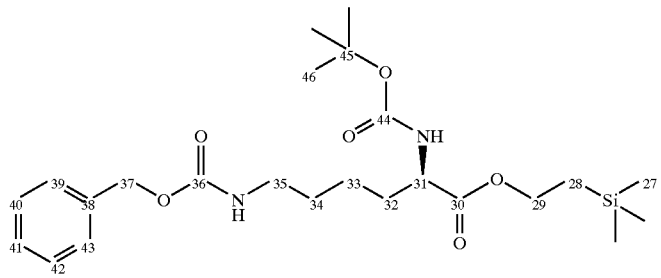

Synthesis of Compound D-14

To a stirred solution of 6-benzyloxycarbonylamino-2-tert-butoxycarbonyl-D-amino-hexanoic acid (17.5 g, 46.0 mMol), DMAP (0.56 g, 4.60 mMol) and 2-trimethylsilylethanol (5.44 g, 46.0 mMol) in CH$_2$Cl$_2$ (250 mL), DCC (10.44 g, 50.6 mMol) was added at 0° C. under N$_2$ atmosphere. After 15 min at 0° C., the solution was stirred at rt for an additional 7.5 h. The solution was filtered to remove the DCU formed and concentrated under reduced pressure (rotavap). D-14 was obtained as a colorless viscous liquid ($C_{24}H_{40}N_2O_6Si$, 20.23 g, 92%) after gravity silica gel chromatography (0 to 5% EA/Hex). $R_f$=0.57 (30% EA/Hex). $^1$H-NMR (300 MHz, CDCl$_3$) δ (ppm): 7.16 ($C_{39}$H—$C_{43}$H, br, s, 5H), 5.57 ($C_{37}$H, s, 2H), 5.39 ($C_{31}$NH, d, J=8.0 Hz, 1H), 4.92 ($C_{31}$H, s, 1H), 4.05 ($C_{29}$H, t, J=9.0 Hz, 2H), 2.99 ($C_{35}$H, d, J=5.7 Hz, 2H), 1.61–1.13 ($C_{32}$H, $C_{33}$H, $C_{34}$H, m, 6H,), 1.28 ($C_{46}$H, s, 9H), 0.84 ($C_{28}$H, t, J=9.0 Hz, 2H), -0.102 ($C_{27}$H, s, 9H). $^{13}$C-NMR (75 MHz, CDCl$_3$) δ (ppm): 172.94 ($C_{30}$), 155.66 ($C_{44}$), 155.60 ($C_{36}$), 136.78 ($C_{38}$), 128.35, 127.93, 127.87 ($C_{39}$–$C_{43}$), 79.38

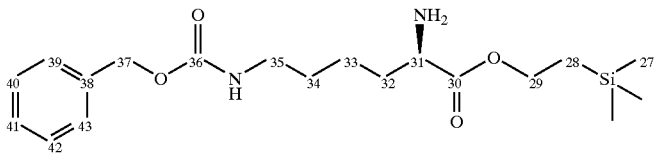

Synthesis of Compound D-15

A solution of compound D-14 (1.6 g, 3.30 mMol) in 10% TFA/CH$_2$Cl$_2$ (50 mL) was stirred at rt under N$_2$ atmosphere for 1.5 h then the excess TFA and solvent was removed under reduced pressure (rotavap). The resulting viscous material was dissolved in CH$_2$Cl$_2$ (50 mL) and concentrated once again under reduced pressure (rotavap) to yield the TFA salt of compound D-15 (C$_{19}$H$_{32}$N$_2$O$_4$Si·CF$_3$CO$_2$H, 1.59 g, 96%) as a colorless foam. This compound was used in the next step without further purification. R$_f$=0.5 (10% CH$_3$OH/CHCl$_3$). $^1$H-NMR (300 MHz, CDCl$_3$) δ (ppm): 8.85 (TFA, br, s, 4H), 8.20 (NHC$_{31}$, br, s, 2H), 7.35–7.30 (C$_{39}$H—C$_{43}$H, m, 5H), 5.09 (C$_{37}$H, s, 2H), 4.32 (C$_{29}$H, t, J=4.0 2H), 4.02 (C$_{31}$H, br, m, 1H), 3.18 (C$_{35}$H, br, s, 2H), 1.98 (C$_{32}$H, br, s, 2H), 1.57–1.46 (C$_{33}$H, C$_{34}$H, m, 4H), 1.07 (C$_{28}$H, t, J=4.4 Hz, 2H), 0.07 (C$_{27}$H, s, 9H). $^{13}$C-NMR (75 MHz, CDCl$_3$) δ (ppm): 169.79 (C$_{30}$), 157.87 (C$_{36}$), 136.45 (C$_{38}$), 128.74, 128.42, 127.95 (C$_{39}$–C$_{43}$), 67.19 (C$_{37}$), 65.87 (C$_{29}$), 53.44 (C$_{31}$), 40.36 (C$_{35}$), 29.88 (C$_{32}$), 29.13 (C$_{34}$), 21.87 (C$_{33}$), 17.37 (C$_{28}$), –1.88 (C$_{27}$). Cl-MS: Expected mass for (M+H$^+$)/z, 381.21. Observed, 381 ((M+H$^+$)/z, 26%).

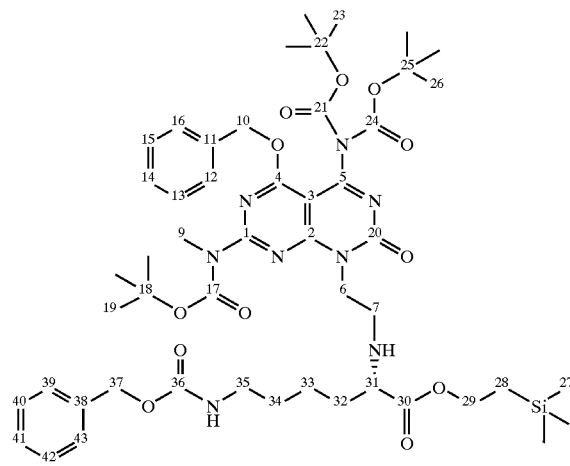

Synthesis of Compound L-16

To a stirred solution of L-15 (TFA salt, 0.8 g, 1.53 mMol) and DIEA (0.53 mL, 0.39 g, 3.07 mMol) in 1,2-DCE (30 mL), a solution of compound 13 (0.98 g, 1.53 mMol) in 1,2-DCE (20 mL) was added at rt under N$_2$ atmosphere. After stirring for 15 min at rt, solid NaB(OAc)$_3$H (0.48 g, 2.3 mMol) was added (Abdel-Magid, J. Org. Chem. 1996, 61, 3849–3862 incorporated herein by reference). The resulting solution was stirred for 16 h at rt then quenched with dH$_2$O (10 mL). The aqueous layer was extracted with CHCl$_3$ (200 mL) and the organic layers were combined, washed with 10% aqueous citric acid (50 mL), dH$_2$O (2×50 mL) and brine (50 mL), then dried over anhydrous Na$_2$SO$_4$. Filtration and evaaporation of the solvent under reduced pressure (rotavap) followed by gravity silica gel chromatography (5 to 20% EA/Hex) yielded compound L-16 as a colorless foam (C$_{50}$H$_{72}$N$_8$O$_{12}$Si, 1.11 g, 72%). R$_f$=0.25 (30% EA/Hex). $^1$H-NMR (500 MHz, CDCl$_3$) δ (ppm): 7.38–7.27 (C$_{15}$H and C$_{13}$H, m, 2H), 7.26–7.19 (C$_{39}$H—C$_{43}$H, C$_{12}$H, C$_{16}$H, C$_{14}$H, br, m, 8H), 5.49 (C$_{10}$H, s, 2H), 5.09 (NHC$_{35}$, m, 1H,), 4.99 (C$_{37}$H, s, 2H), 4.35 (C$_6$H, t, J=6.5 Hz, 2H), 4.10 (C$_{29}$H, t, J=8.5 Hz, 2H), 3.40 (C$_9$H, s, 3H), 3.15 (C$_7$H, t, J=6.5 Hz, 1H), 3.05–3.01 (C$_7$H, C$_{35}$H, br, m, 3H), 2.75 (C$_{31}$H, br, q, 1H), 1.52 (C$_{19}$H, s, 9H), 1.39–1.16 (C$_{32}$H, C$_{33}$H, C$_{34}$H, br, m, 6H), 1.25 (C$_{23}$H, C$_{26}$H, s, 18H), 0.91 (C$_{28}$H, t, J=8.5 Hz, 2H), –0.03 (C$_{27}$H, s, 9H). $^{13}$C-NMR (125 MHz, CDCl$_3$) δ (ppm): 175.64 (C$_{30}$), 165.87 (C$_{17}$), 161.37 (C$_{21}$), 161.14 (C$_{24}$), 160.44 (C$_1$), 156.60 (C$_2$), 156.04 (C$_4$), 152.78 (C$_{20}$), 149.53 (C$_5$), 136.95 (C$_{38}$), 135.10 (C$_{11}$), 128.86, 128.74, 128.73, 128.61, 128.55 (C$_{12}$–C$_{16}$), 128.30, 128.20, 128.13 (C$_{39}$–C$_{43}$), 93.04 (C$_3$), 83.89 (C$_{22}$, C$_{25}$), 83.19 (C$_{18}$), 70.22 (C$_{10}$), 66.55 (C$_{37}$), 63.04 (C$_{29}$), 61.21 (C$_{31}$), 45.40 (C$_6$), 43.07 (C$_7$), 41.00. (C$_{35}$), 35.05 (C$_9$), 33.12 (C$_{32}$), 29.79 (C$_{34}$), 28.29 (C$_{19}$), 27.97 (C$_{23}$, C$_{26}$), 23.15 (C$_{33}$), 17.66 (C$_{28}$), –1.30 (C$_{27}$). PD-MS: Expected mass for (M+H$^+$)/z, 1005.5. Observed, 1007 ((M+H$^+$)/z), 805 ((M+H$^+$)/z-2Boc), 705 ((M+H$^+$)/z-3Boc). Positive ESI-MS: Expected mass for (M+H$^+$)/z, 1005.5. Observed, 1005.3 ((M+H$^+$)/z, 100%), 805.3 ((M+H$^+$)/z-2Boc, 9%), 705.4 ((M+H$^+$)/z-3Boc, 7%). Positive high resolution ESI-MS: Expected mass for (M+H$^+$)/z, 1005.5117. Observed, 1005.5101.

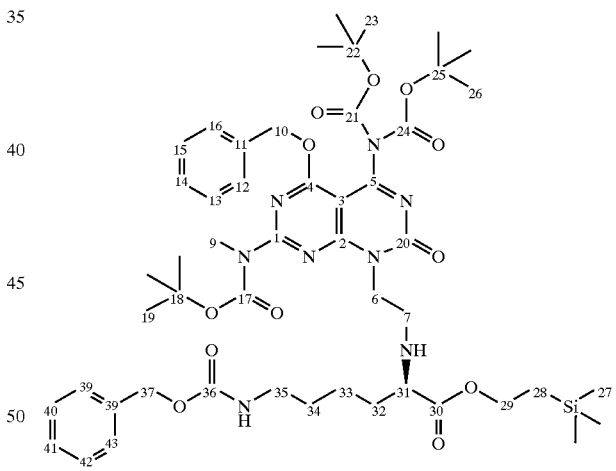

Synthesis of Compound D-16

To a stirred solution of D-15 (TFA salt, 0.70 g, 1.34 mMol) and DIEA (0.60 mL, 0.45 g, 3.44 mMol) in 1,2-DCE (25 mL), a solution of compound 13 (0.86 g, 1.34 mMol) in 1,2-DCE (25 mL) was added at rt under N$_2$ atmosphere. After stirring for 15 min at rt, solid NaB(OAc)$_3$H (0.54 g, 2.58 mMol) was added. The resulting solution was stirred for 16 h at rt then quenched with dH$_2$O (10 mL). The aqueous layer was extracted with CHCl$_3$ (200 mL) and the organic layers were combined, washed with 10% aqueous citric acid (50 mL), dH$_2$O (2×50 mL) and brine (50 mL), then dried over anhydrous Na$_2$SO$_4$. Filtration and evaporation of the solvent under reduced pressure (rotavap) followed by gravity silica gel chromatography (5 to 20%

EA/Hex) yielded compound D-16 as a colorless foam ($C_{50}H_{72}N_8O_{12}Si$, 0.95 g, 70%). $R_f$=0.25 (30% EA/Hex). mp=52° C. $^1$H-NMR (500 MHz, $CDCl_3$) δ (ppm): 7.39–7.27 ($C_{15}H$, $C_{13}H$, m, 2H), 7.26–7.18 ($C_{39}H$—$C_{43}H$, $C_{12}H$, $C_{16}H$, $C_{14}H$, br, m, 8H), 5.50 ($C_{10}H$, s, 2H), 5.09 ($C_{35}NH$, m, 1H), 5.00 ($C_{37}H$, S, 2H), 4.36 ($C_6H$, t, J=6.5 Hz, 2H), 4.10 ($C_{29}H$, t, J=9 Hz, 2H), 3.40 ($C_9H$, s, 3H), 3.16 ($C_7H$, t, J=6.5 Hz, 1H), 3.06–2.97 ($C_7H$, $C_{35}H$, br, m, 3H), 2.76 ($C_{31}H$, br, q, 1H), 1.52 ($C_{19}H$, s, 9H), 1.39–1.13 ($C_{32}H$, $C_{33}H$, $C_{34}H$, br, m, 6H), 1.26 ($C_{23}H$, $C_{26}H$, s, 18H), 0.92 ($C_{28}H$, t, J=8.5 Hz, 2H), -0.03 ($C_{27}H$, s, 9H). $^{13}$C-NMR (125 MHz, $CDCl_3$) δ (ppm): 175.64 ($C_{30}$), 165.87 ($C_{17}$), 161.37 ($C_{21}$), 161.14 ($C_{24}$), 160.45 ($C_1$), 156.60 ($C_2$), 156.04 ($C_4$), 152.77 ($C_{20}$), 149.54 ($C_5$), 136.96 ($C_{38}$), 135.11 ($C_{11}$), 128.86, 128.75, 128.73, 128.61, 128.55 ($C_{12}$–$C_{16}$), 128.30, 128.20, 128.13 ($C_{39}$–$C_{43}$), 93.04 ($C_3$), 83.89 ($C_{22}$), 83.87 ($C_{25}$), 83.19 ($C_{18}$), 70.23 ($C_{10}$), 60.55 ($C_{37}$), 63.04 ($C_{29}$), 61.22 ($C_{31}$), 45.41 ($C_6$), 43.07 ($C_7$), 41.01 ($C_{35}$), 35.05 ($C_9$), 33.12($C_{32}$), 29.80 ($C_{34}$), 28.29 ($C_{19}$), 27.98 ($C_{23}$, $C_{26}$), 23.15 ($C_{33}$), 17.67 ($C_{28}$), -1.30 ($C_{27}$). Positive ESI-MS: Expected mass for (M+H$^+$)/z, 1005.5. Observed, 1005.2 ((M+H$^+$)/z, 100%), %), 805.2 ((M+H$^+$)/z-2Boc, 30%), 705.3 ((M+H$^+$)/z-3Boc, 10%).

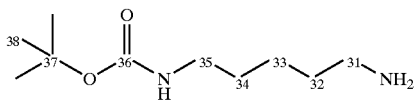

Synthesis of Compound 17

To a stirred solution of 1,5-diaminopentane (4.5 g, 44.0 mMol) in dioxane (15 mL), a solution of $Boc_2O$ (1.23 g, 5.5 mMol) in dioxane (15 mL) was slowly added at rt over a period of 2.5 h. After stirring for 22 h the solvent was removed under reduced pressure (rotovap), $dH_2O$ (25 mL) was added and the resulting precipitate (undesired bis-N-Boc-2,5-diaminopentane) was filtered. The filtrate was extracted with $CH_2Cl_2$ (3×50 mL) and the combined organic layers were evaporated under reduced pressure. Compound 17 ($C_{10}H_{22}N_2O_2$, 0.88 g, 80%) was obtained as a viscous liquid, which was used in the next step without further purification. $R_f$=0.47 (10% $CH_3OH/CHCl_3$). $^1$H-NMR (200 MHz, $CDCl_3$) δ (ppm): 4.90 ($NHC_{35}$, br, s, 1H), 3.03 ($C_{35}H$, br, s, 2H), 2.62 ($C_{31}H$, br, s, 2H), 1.37 ($C_{38}H$, $C_{32}H$, $C_{33}H$, $C_{34}H$, br, s, 15H,), 1.08 ($NHC_{31}$, br, s, 2H).

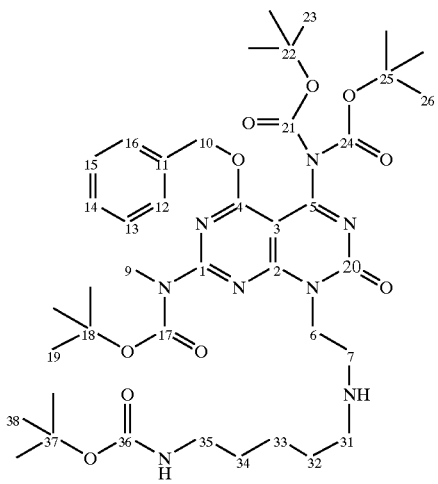

Synthesis of Compound 18

To a stirred solution of 17 (0.20 g, 1.0 mMol) and compound 13 (0.64 g, 1.0 mMol) in 1,2-DCE (30 mL), Na(AcO)$_3$BH (0.32 g, 1.5 mMol) was added at rt under $N_2$ atmosphere. The resulting solution was stirred 12 h, at rt then quenched with $dH_2O$ (10 mL). The aqueous layer was extracted with $CHCl_3$ (45 mL) and the organic layers were combined and washed successively with 10% aqueous citric acid (50 mL), $dH_2O$ (2×50 mL) and brine (50 mL), then dried over anhydrous $Na_2SO_4$. Filtration and evaporation of the solvent under reduced pressure (rotavap) followed by gravity silica gel chromatography (5 to 20% EA/Hex) yielded compound 18 as a colorless foam ($C_{41}H_{62}N_8O_{10}$, 0.46 g, 55%). $R_f$=0.44 (2% $CH_3OH/CHCl_3$). $^1$H-NMR (300 MHz, $CDCl_3$) δ (ppm): 7.48–7.36 ($C_{12}H$–$C_{16}H$, m, 5H), 5.59 ($C_{10}H$, S, 2H), 4.59 ($NHC_{31}$, br, s, 1H), 4.48 ($C_6H$, t, 2H, J=6.6 Hz), 3.49 ($C_9H$, s, 3H), 3.01 ($C_7H$, t, J=6.6 Hz, 2H), 2.65 ($C_{31}H$, t, J=6.9 Hz, 2H), 1.61 ($C_{38}H$, s, 9H), 1.46 ($C_{19}H$, s, 9H), 1.35 ($C_{23}H$ and $C_{26}H$, s, 18H), 0.88 ($C_{34}H$, q, J=14.1 and 6.0 Hz, 2H). Positive ESI-MS: Expected mass for (M+H$^+$)/z, 827.47. Observed, 827.3 ((M+H$^+$)/z, 100%), 727.2 ((M+H$^+$)/z, -Boc, 8%), 627.3 ((M+H$^+$)/z, -2Boc, 13%), 527.3 ((M+H$^+$)/z, -3Boc, 17%), 427.3 ((M+H$^+$)/z, -4Boc, 31%). Negative ESI-MS: Expected mass for (M+H$^+$)/z, 825.46. Observed, 825.4 ((M–H$^+$)/z, 73%). Positive high resolution ESI-MS: Expected mass for (M+H$^+$)/z, 827.4667. Observed, 827.4659.

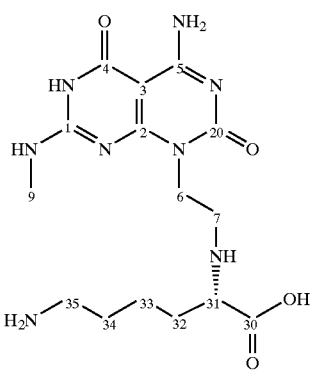

Synthesis of L-module 1

A 94% solution of TFA/thioanisole (10 mL) was added to L-16 (0.48 g, 0.48 mMol) at rt under $N_2$ atmosphere. After stirring for 60 h at rt, $Et_2O$ (50 mL) was added. The precipitate formed was centrifuged and washed with $Et_2O$ (3×10 mL), redissolved in TFA (15 mL), reprecipitated with $Et_2O$ (20 mL) then washed with $Et_2O$ (2×10 mL) and $CH_3OH$ (10 mL). L-Module 1 was obtained as a white solid ($C_{15}H_{24}N_8O_4$—$(CF_3CO_2H)_{2.5}$—$(H_2O)_{1.5}$, 0.168 g, 45%). mp>298° C. (decomposed). $^1$H-NMR (600 MHz, 90% $H_2O$/$D_2O$) δ (ppm): 9.15 ($C_5NH_2$, br, s, 2H), 8.34 ($C_4NH$, br, s, 1H), 7.57 ($C_9NH$, br, m, 1H), 7.39 ($C_{35}NH$, br, s, 3H, protonated ammonium), 3.81 ($C_{31}H$, t, J=5.0 Hz, 1H), 3.36 ($C_7H$, t, J=6.0 Hz, 2H), 2.90 ($C_9H$, br, m, 3H), 2.85 ($C_{35}H$, br, m, 2H), 1.84–1.79 ($C_{32}H$, m, 2H), 1.55 ($C_{34}H$, br, s, 2H), 1.36 ($C_{33}H$, br, m, 1H), 1.29 ($C_{33}H$, br, m, 1H). $C_6H$ was suppressed with the solvent peak. $^1$H-NMR (DMSO-$d_6$, 500 MHz) δ (ppm): 12.60 ($C_{30}OH$ or $C_{31}NH$, br, s, 1H), 9.76 ($C_5NH$, s, 1H), 9.19 ($C_5NH$ and $C_4NH$, s, 2H), 8.74 ($C_9NH$, m, 1H), 7.83 ($C_{35}NH$, br, s, 3H, protonated ammonium), 4.41–4.32 ($C_6H$, m, 2H), 3.98 ($C_{31}H$, br, s, 1H), 3.29 ($C_7H$, br, m, 2H), 2.94 ($C_9H$, br, m, 3H), 2.74 ($C_{35}H$, br, m, 2H), 1.86 ($C_{32}H$, m, 1H), 1.77 ($C_{32}H$, m, 1H), 1.53 ($C_{34}H$, m, 2H), 1.43 ($C_{33}H$, m, 1H), 1.29 ($C_{33}H$, m, 1H). $^{13}$C-NMR (125 MHz, $D_2O$ and a drop of TFA) δ (ppm): 171.08 ($C_{30}$), 162.60 (TFA), 160.39 ($C_4$), 155.87 ($C_5$), 155.73 ($C_{20}$), 149.77 ($C_2$), 118.39 ($C_1$), 114.54 ($CF_3$ from TFA), 82.94 ($C_3$), 60.04 ($C_{31}$), 44.33 ($C_6$), 39.17 ($C_7$), 38.90 ($C_{35}$), 28.03

($C_{34}$), 26.44 ($C_{32}$), 26.37 ($C_{33}$), 21.52 ($C_9$). Positive ESI-MS: Expected mass for (M+H$^+$)/z, 381.19. Observed, 381.20 ((M+H$^+$)/z, 100%). Negative ESI-MS: Expected mass for (M–H$^+$)/z, 379.19. Observed, 379.30. ((M–H$^+$)/z, 100%). High resolution ESI-MS: Expected mass for (M+H$^+$)/z, 381.1999. Observed, 381.2003. Elemental analysis: Calculated for [$C_{15}H_{24}N_8O_4$—(CF$_3$CO$_2$H)$_{2.5}$—(H$_2$O)$_{1.5}$]: C, 34.69; H, 4.2; N, 16.18; F: 20.58. Found: C, 34.99; H, 4.16; N, 15.96; F, 20.26.

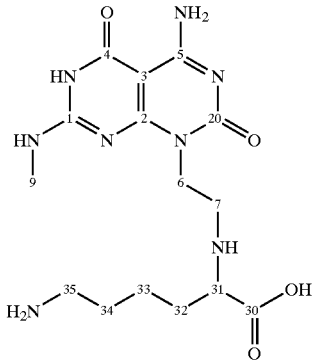

Synthesis of D-module 1

A 94% solution of TFA/thioanisole (15 mL) was added to D-16 (0.93 g, 0.93 mMol) at rt under N$_2$ atmosphere. After stirring for 86 h at rt, Et$_2$O (50 mL) was added. The precipitate formed was centrifuged and washed with Et$_2$O (3×10 mL), redissolved in TFA (15 mL), reprecipitated with Et$_2$O (20 mL) then washed with Et$_2$O (2×10 mL) and CH$_3$OH (10 mL). D-Module 1 was obtained as a white solid ($C_{15}H_{24}N_8O_4$—CF$_3$CO$_2$H)$_{2.5}$—(H$_2$O)$_{1.5}$, 0.36 g, 50%). mp>298° C. (decomposed). $^1$H-NMR (DMSO-d$_6$, 500 MHz) δ (ppm): 12.56 ($C_{30}$OH or $C_{31}$NH, br, s, 1H), 9.48 ($C_5$NH, s, 1H), 9.23 ($C_5$NH and $C_4$NH, s, 2H), 8.61 ($C_9$NH, m, 1H), 7.79 ($C_{35}$NH, br, s, 3H, protonated ammonium), 4.41–4.32 ($C_6$H, m, 2H), 3.99 ($C_{31}$H, br, s, 1H), 3.31 ($C_7$H, br, m, 2H), 2.95 ($C_9$H, br, m, 3H), 2.76 ($C_{35}$H, br, m, 2H), 1.86 ($C_{32}$H, m, 1H), 1.77 ($C_{32}$H, m, 1H), 1.54 ($C_{34}$H, m, 2H), 1.43 ($C_{33}$H, m, 1H), 1.30 ($C_{33}$H, m, 1H). $^{13}$C-NMR (125 MHz, D$_2$O) δ (ppm): 172.19 ($C_{30}$), 162.47 (TFA), 160.2 ($C_4$), 155.67 ($C_5$), 155.46 ($C_{20}$), 149.69 ($C_2$), 117.42 ($C_1$), 115.09 (CF$_3$ from TFA), 82.74 ($C_3$), 61.32 ($C_{31}$), 44.25 ($C_6$), 38.89 ($C_7$), 38.68 ($C_{35}$), 28.51 ($C_{34}$), 27.62 ($C_{32}$), 26.37 ($C_{33}$), 21.32 ($C_9$). Positive ESI-MS: Expected mass for (M+H$^+$)/z, 381.19. Observed, 381.1 ((M+H$^+$)/z, 100%).

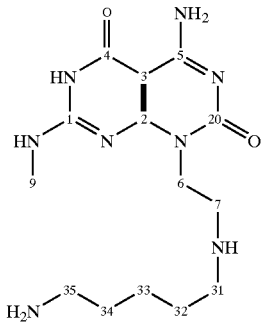

Synthesis of Module 4

A 94% solution of TFA/thioanisole (7.5 mL) was added to 18 (0.4 g, 0.48 mMol) at rt under N$_2$ atmosphere. After stirring for 4 h at rt, Et$_2$O (50 mL) was added. The precipitate formed was centrifuged and washed with Et$_2$O (3×10 mL), redissolved in TFA (15 mL), reprecipitated with Et$_2$O (20 mL) then washed with Et$_2$O (2×10 mL) and CH$_3$OH (10 mL). Module 4 was obtained as a white solid ($C_{14}H_{24}N_8O_4$—(CF$_3$CO$_2$H)$_2$—(H$_2$O)$_{1.5}$, 0.21 g, 77%). mp=130° C. $^1$H-NMR (500 MHz, 90% H$_2$O/D$_2$O) δ (ppm): 9.14 ($C_5$NH, br, s, 2H,), 8.32 ($C_4$NH, br, m, 1H), 7.53–7.29 ($C_7$NH, $C_9$NH, $C_{35}$NH, m, 4H), 3.30 ($C_7$H, s, 2H), 2.93–2.83 ($C_9$H, $C_{31}$H, $C_{35}$H, m, 7H), 1.55–1.50 ($C_{32}$, $C_{34}$H, m, 4H), 1.28 ($C_{33}$H, t, J=4.8Hz, 2H). $C_6$H suppressed with the solvent. $^{13}$C-NMR (75 MHz, D$_2$O) δ (ppm): 163.6–163.2 (TFA), 160.42 ($C_4$), 155.92 ($C_{20}$), 155.74 ($C_5$), 149.89 ($C_2$), 118.48 ($C_1$), 114.61 (CF$_3$ from TFA), 82.92 ($C_3$), 47.92 ($C_6$), 45.80 ($C_7$), 39.31 ($C_{31}$, $C_{35}$), 27.98 ($C_{32}$), 26.41 ($C_{33}$), 25.16 ($C_{34}$), 22.92 ($C_9$). Positive ESI-MS: Expected mass for (M+H$^+$)/z, 337.20. Observed 337.2 ((M+H$^+$)/z, 100%). Negative ESI-MS: Expected mass for (M–H$^+$)/z, 335.20. Observed 335.3 ((M–H$^+$)/z, 20%).

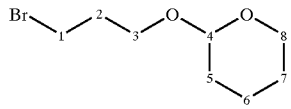

Synthesis of Compound 19

3-bromo-1-propanol (10 g, 71.9 mMol) was cooled to 0° C. in a single-neck round-bottom flask (100 mL), and DHP (7.22 mL, 79.1 mMol) was added dropwise. 12 M HCl (2 drops) was added, and the reaction mixture was stirred at rt for 2 h. The reaction was quenched with Na$_2$CO$_3$ (1.0 g), and the solid was filtered and washed with CH$_2$Cl$_2$ (20 mL). The filtrate was evaporated under reduced pressure (rotavap), and the residual oil was purified by low-pressure short path distillation (0.05 mm Hg). Compound 19 ($C_8H_{15}BrO_2$, 15.0 g, 94%) was obtained as a colorless oil. R$_f$=0.45(10% EA/Hex). $^1$H NMR (CDCl$_3$, 200 MHz) δ (ppm): 4.60 ($C_4$H, t, J=3.4Hz, 1H), 3.84 ($C_8$H, m, 2H), 3.43–3.54 ($C_1$H, $C_3$H m, 4H), 2.10 ($C_2$H, m, 2H), 1.49–2.0 ($C_5$H–$C_7$H, m, 6H). 13C NMR (CDCl$_3$, 50 MHz) δ (ppm): 98.78 ($C_4$), 64.77 ($C_8$), 62.14 ($C_3$), 32.82, 30.58, 30.50, 25.33, 19.39 ($C_1$, $C_2$, $C_5$—$C_7$).

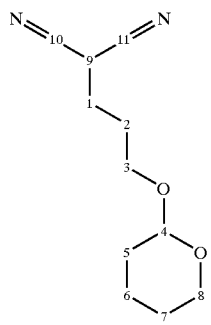

Synthesis of Compound 20

Malononitrile (8.88 g, 135 mMol) in DME (63 mL) was added dropwise to a suspension of 95% NaH (1.93 g, 80.4 mMol) and DME (30 mL) in a three-neck round-bottom flask (500 mL). Compound 19 (15.0 g, 67.0 mMol) in DME (14 mL) was added dropwise, and the reaction mixture was stirred at rt overnight under N$_2$ atmosphere. The reaction was quenched with 5% aqueous NH$_4$Cl until pH~8. The reaction mixture was diluted with EA (100 mL) and washed with dH$_2$O (3×200 mL) and brine (100 mL). The organic layer was dried over anhydrous Na$_2$SO$_4$, filtered, and the solvents were evaporated under reduced pressure (rotavap). Compound 20 ($C_{11}H_{16}N_2O_2$, 12.2 g, 88%) was obtained as a colorless oil after silica gel flash chromatography (0–15% Et$_2$O/Hex). R$_f$=0.35 (70% Et$_2$O/Hex). $^1$H NMR (CDCl$_3$, 200 MHz) δ (ppm): 5.00 ($C_4$H, t, J=2.8Hz, 1H), 4.00 ($C_9$H, t, J=7.2Hz, 2H), 3.77 ($C_8$H, m, 2H), 3.45 ($C_3$H, p, J=5.3Hz, 2H), 2.12 (C₁H, q, J=7.5Hz, 2H), 1.46–1.90 (C₅H–C₇H, C₂H m, 8H). ¹³C NMR (CDCl₃, 50 MHz) δ (ppm): 112.77 (C₁₀, C₁₁), 98.86 (C₄), 65.56 (C₈), 62.43 (C₃), 30.34, 28.48, 26.04, 25.03, 22.10, 19.44 (C₁, C₂, C₅–C₇, C₉). Cl-MS: Expected mass for (M+H⁺)/z, 209.12. Observed, 209 ((M+H⁺)/z, 67%),125 ((M+H⁺)/z —CH₂CH₂CH₂OTHP, 10%). Positive high resolution Cl-MS: Expected mass for (M+H⁺)/z, 208.1212. Observed, 208.1217.

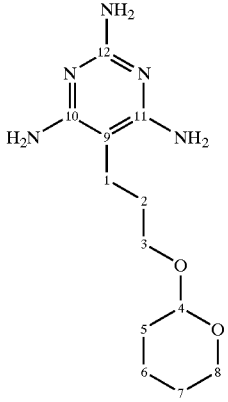

Synthesis of Compound 21

EtOH (250 mL) and sodium (2.71 g, 118 mMol) were stirred in a two-neck round-bottom flask (500 mL) under N₂ atmosphere until dissolution of the sodium. The solution was transferred to compound 20 (12.2 g, 58.6 mMol) and guanidinium hydrochloride (6.71 g, 70.3 mMol) in a three-neck round-bottom flask (500 mL), and the reaction mixture was refluxed for 5 h under N₂ atmosphere. The reaction was then cooled to rt and quenched with 1M aqueous HCl until pH~8. The solvents were evaporated under reduced pressure (rotavap) to yield compound 21 (C₁₂H₂₁N₅O₂, 9.15 g, 74%) as a light yellow solid after silica gel flash chromatography (0–10% MeOH/CH₂Cl₂). R_f=0.08 (10% MeOH/ CH₂Cl₂). mp=170° C. ¹H NMR (DMSO-d₆, 200 MHz) δ (ppm): 7.17 (C₁₂NH, s, 2H), 7.04 (C₁₀NH, C₁₁NH, s, 4H), 4.52 (C₄H, m, 1H), 3.70 (C₈H, m, 2H), 3.46 (C₃H, m, 2H), 2.28 (C₁H, m, 2H), 1.45–1.73 (C₅H–C₇H, C₂H, m, 8H). ¹³C NMR (DMSO-d₆, 50 MHz) δ (ppm): 208.04 (C₁₀, C₁₁), 152.41 (C₁₂), 99.34, 83.58 (C₄, C₉), 61.66, 66.20 (C₃, C₈), 56.05, 30.46, 27.42, 25.07, 19.43 (C₁, C₂, C₅–C₇). Cl-MS: Expected mass for (M+H⁺)/z, 268.17. Observed, 268 ((M+H⁺)/z, 100%), 184 ((M+H⁺)/z-THP, 28%). Positive high resolution FAB-MS (KIPEG, NBA): Expected mass for (M+H⁺)/z, 268.1774. Observed, 268.1786.

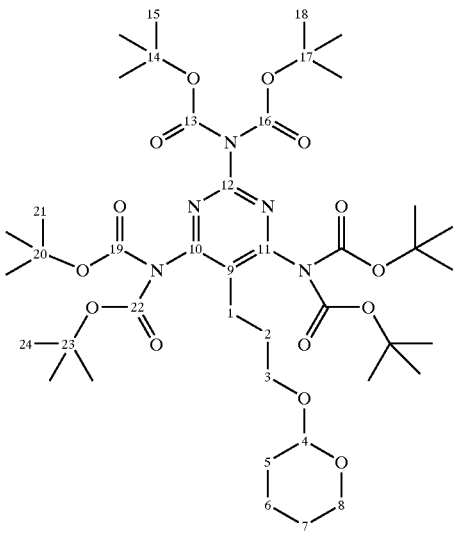

Synthesis of Compound 22

Compound 21 (2.0 g, 7.44 mMol), THF (200 mL), Boc₂O (11.43 g, 52.4 mMol), Et₃N (8.34 mL, 59.9 mMol), and DMAP (0.64 g, 5.24 mMol) were stirred in a single-neck round-bottom flask (500 mL) overnight at rt under N₂ atmosphere. The reaction was quenched with 5% aqueous NaHCO₃ (5 mL), and the THF was evaporated under reduced pressure (rotavap). The resulting material was dissolved in Et₂O (100 mL), and the organic layer was washed with 5% aqueous NaHCO₃ (2×100 mL), dH₂O (100 mL) and brine (50 mL). The organic layer was dried over anhydrous Na₂SO₄, filtered, and the Et₂O was evaporated under reduced pressure (rotavap). Compound 22 (C₄₂H₆₉N₅O₁₄, 2.9 g, 45%) was obtained as a foam after silica gel flash chromatography (0–15% EA/Hex). R_f=0.29 (20% EA/Hex). mp=104° C. ¹H NMR (CDCl₃, 200 MHz) δ (ppm): 4.58 (C₄H m, 1H), 3.74 (C₈H, m, 2H), 3.44 (C₃H m, 1H), 2.58 (C₁H, m, 2H), 1.10–1.90 (C₁₅H, C₁₈H, C₂₁H, C₂₄H, C₅H–C₇H, C₂H, m, 62H). ¹³C NMR (CDCl₃, 125 MHz) δ (ppm): 161.28 (C₁₀, C₁₁), 155.45 (C₁₂), 150.09 (C₁₃, C₁₈), 149.48 (C₁₉, C₂₂), 127.66 (C₉), 97.88 (C₄), 83.38 (C₂₀, C₂₃), 82.77 (C₁₄, C₁₇), 65.89, 61.47 (C₃, C₈), 27.30 (C₂₁, C₂₄), 27.25 (C₁₅, C₁₈), 30.16, 25.03, 23.07, 22.13, 18.86 (C₁, C₂, C₅–C₇). Cl-MS: Expected mass for (M+H⁺)/z, 868.49. Observed, 868 ((M+H⁺)/z, 4%), 784 ((M+H⁺)/z-THP, 3%), 768 ((M+H⁺)/z-Boc, 9%), 694 ((M+H⁺)/z-2Boc-THP, 20%,). Positive high resolution FAB-MS (KIPEG, NBA): Expected mass for (M+H⁺)/z, 868.4919. Observed, 868.4903.

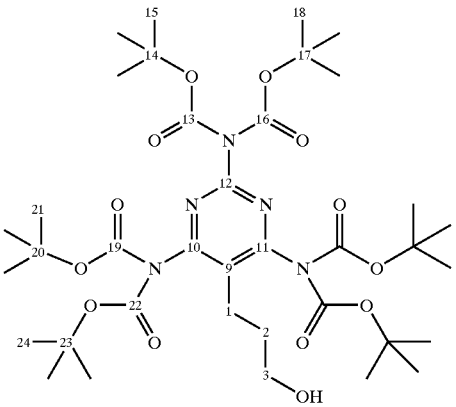

Synthesis of Compound 23

Compound 22 (2.8 g, 3.22 mMol), MeOH (100 mL) and pTsOH (0.06 g, 0.32 mMol) were stirred in a single-neck round-bottom flask (250 mL) for 5 h under N₂ atmosphere. The reaction was quenched with 5% aqueous NaHCO₃ (3 mL), and the solvents were evaporated under reduced pressure (rotavap). The solid material was dissolved in Et₂O (100 mL) and washed with 5% aqueous NaHCO₃ (5×100 mL), dH₂O (100 mL), and brine (50 mL). The organic layer was dried over anhydrous Na₂SO₄, filtered, and the solvent was evaporated under reduced pressure (rotavap) to give compound 23 (C₃₇H₆₁N₅O₁₃, 2.47 g, 98%) as a foam. R_f=0.13 (30% EA/Hex). mp=148° C. ¹H NMR (CDCl₃, 200 MHz) δ (ppm): 3.55 (C₃H, m, 2H), 2.59 (C₁H, t, J=7.8Hz, 2H), 1.81 (C₂H, m, 2H), 1.5–1.6 (C₁₅H, C₁₈H, C₂₁H, C₂₄H, m, 54H). 13C NMR (CDCl₃, 50 MHz) δ (ppm): 161.39 (C₁₀, C₁₁), 155.57 (C₁₂), 150.17 (C₁₃, C₁₆), 149.98 (C₁₉, C₂₂), 127.49 (C₉), 83.83 (C₂₀, C₂₃), 83.05 (C₁₄, C₁₇), 61.22 (C₃), 29.98 (C₂), 27.44 (C₁₅, C₁₈, C₂₁, C₂₄), 22.54 (C₁). Cl-MS: Expected mass for (M+H⁺)/z, 783.43. Observed, 783 ((M+H⁺)/z), 684 ((M+H⁺)/z-Boc). Positive high resolution FAB- MS (KIPEG, NBA): Expected mass for $(M+H^+)/z$, 784.4344. Observed, 784.4323.

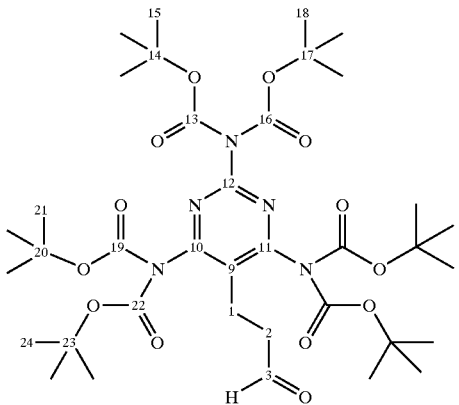

Synthesis of Compound 24

Compound 23 (0.20 g, 0.26 mMol), $CH_2Cl_2$ (10 mL) and Dess-Martin periodinane (0.22 g, 0.51 mMol) (Dess J. Org. Chem. 1983, 48, 4155–4156, incorporated herein by refernce.) were stirred in a single-neck round-bottom flask (50 mL) at rt for 2 h. The reaction was quenched with 5% aqueous $NaHCO_3$ (2 mL), diluted with $CH_2CO_2$ (50 mL) and washed with 5% aqueous $NaHCO_3$ (10×50 mL) and brine (50 mL). The organic layer was dried over anhydrous $Na_2SO_4$, filtered, and the solvent was evaporated under reduced pressure (rotapvap) to give compound 24 ($C_{37}H_{59}N_5O_{13}$, 0.19 g, 94%) as a foam. $R_f$=0.34 (30% EA/Hex). mp=98–99° C. $^1H$ NMR ($CDCl_3$, 200 MHz) δ (ppm): 9.77 ($C_3H$, s, 1H), 2.77 ($C_1H$, m, 2H), 1.2–1.28 (58H, $C_{15}H$, $C_{17}H$, $C_{21}H$, $C_{24}H$, $C_2H$, m). $^{13}C$ NMR ($CDCl_3$, 50 MHz) δ (ppm): 200.00 ($C_3$), 162.11 ($C_{10}$, $C_{11}$), 156.77 ($C_{12}$), 150.91 ($C_{13}$, $C_{16}$), 150.33 ($C_{19}$, $C_{22}$), 127.19 ($C_9$), 84.62 ($C_{20}$, $C_{23}$), 83.94 ($C_{14}$, $C_{17}$), 41.93 ($C_2$), 28.14 ($C_{21}$, $C_{24}$), 27.93 ($C_{15}$, $C_{18}$), 19.05 ($C_1$). Cl-MS: Expected mass for $(M+H^+)/z$, 782.42. Observed, 782 (($M+H^+)/z$, 3%), 754 (($M+H^+)/z$-CO, 0.4% 682 (($M+H^+)/z$-Boc, 11%), 582 (($M+H^+)/z$- 2Boc, 4%). Positive high resolution FAB-MS (KIPEG, NBA): Expected mass for $(M+H^+)/z$, 782.4188. Observed, 782.4171.

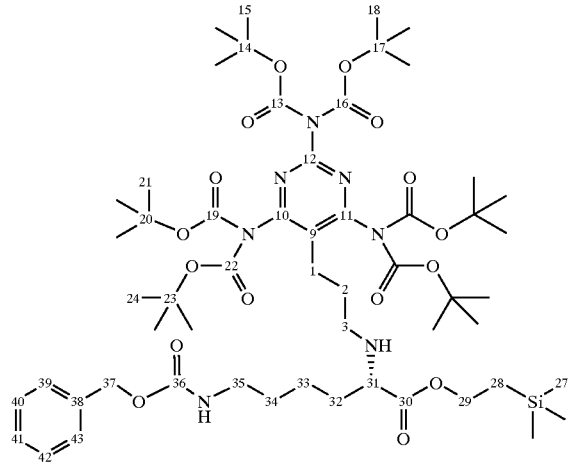

Synthesis of Compound 25

Compound 24 (0.36 g, 0.455 mMol) and $Na(AcO)_3BH$ (0.131 g, 0.621 mMol) were added in one portion to a vigorously stirred solution of L-15 (0.20 g, 0.41 mMol), 1,2-DCE (3 mL) and $Et_3N$ (0.17 mL, 1.24 mMol) in a single neck round-bottom flask (50 mL). The reaction mixture was stirred overnight at rt under $N_2$ atmosphere then quenched with 5% aqueous $NaHCO_3$ (2 mL). $CH_2Cl_2$ (25 mL) was added, and the organic layer was separated and washed with 5% aqueous $NaHCO_3$ (2×25 mL), $dH_2O$ (25 mL) and brine (25 mL), dried over anhydrous $Na_2SO_4$, filtered, and evaporated under reduced pressure (rotavap). Compound 25 ($C_{59}H_{91}N_7O_{16}Si$, 0.22 g, 46%) was obtained as a foam after silica gel flash chromatography (0–20% EA/Hex). $R_f$=0.2 (30% EA/Hex). mp=128° C. (decomposition). $^1H$ NMR ($CDCl_3$, 500 MHz) δ (ppm): 7.27–7.39 ($C_{39}H$–$C_{43}H$, m, 5H), 5.23 ($C_{41}NH$, br, s, 1H), 5.08 ($C_{43}H$, s, 2H), 4.18 ($C_{31}H$, t, J=8Hz, 2H), 3.20 ($C_{36}H$, m, 2H), 3.10 ($C_{38}H$, t, J=6.5Hz, 1H), 2.30–2.55 ($C_1H$, $C_3H$, m, 4H), 1.37–1.48 ($C_{15}H$, $C_{18}H$, $C_{24}H$, $C_{38}H$–$C_{40}H$, $C_2H$, m, 62H), 0.98 ($C_{28}H$, t, J=8.5Hz, 2H), 0.00 ($C_{27}H$, s, 9H). $^{13}C$ NMR ($CDCl_3$, 125 MHz) δ (ppm): 175.96 ($C_{30}$), 161.86 ($C_{10}$, $C_{11}$), 156.72, ($C_{12}$, $C_{36}$), 150.77 ($C_{13}$, $C_{16}$),150.17 ($C_{19}$, $C_{22}$), 130.01 ($C_{38}$), 128.42 ($C_9$), 128.13 ($C_{40}$, $C_{42}$), 128.63 ($C_{39}$, $C_{43}$), 128.21 ($C_{41}$), 84.15 ($C_{20}$, $C_{23}$), 83.50 ($C_{14}$, $C_{17}$), 66.57, 63.05 ($C_{37}$, $C_{29}$), 61.42 ($C_{31}$), 47.67 ($C_3$), 40.96 ($C_{35}$), 33.61 ($C_{32}$), 29.97, 28.21 ($C_2$, $C_{34}$), 28.00, 27.95 ($C_{15}$, $C_{18}$, $C_{21}$, $C_{24}$), 24.37, 23.44 ($C_1$, $C_{33}$) 17.71 ($C_{28}$), -1.31 ($C_{27}$). ESI-MS: Expected mass for $(M+H^+)/z$ 1146.63. Observed, 1146.47.

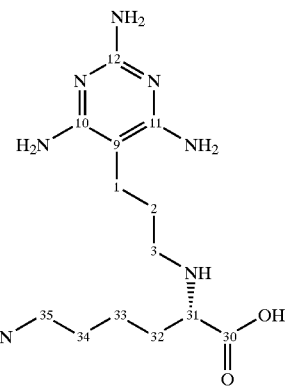

Synthesis of L-module 2

Compound 25 (0.20 g, 0.18 mMol) and 94% TFA/ thioanisole (10 mL) were stirred in a single neck round-bottom flask (50 mL) overnight at rt under $N_2$ atmosphere. The TFA was evaporated and the crude product was suspended in $Et_2O$ (20 mL), centrifuged down (5000 rpm, 10 min), and the solid isolated was resuspended in $Et_2O$ (9 mL). This suspension/centrifugation/isolation procedure was repeated three times. After drying under vacuum, L-module 2 $(C_{13}H_{25}N_7O_2$—$(CF_3CO_2H)_{2.5}$—$(H_2O)_{20}$——$Et_2O)_{0.5}$, 0.10 g, 82%) was obtained as an off-white hygroscopic solid. mp=108° C. $^1H$ NMR (DMSO-$d_6$, 500 MHz) δ (ppm): 8.85–9.10 ($C_{30}OH$, br, 1H,), 7.70–7.90 ($C_{35}NH$, br, 3H), 6.90–7.20 ($C_{10}NH$—$C_{12}NH$, br, 6H), 3.91 ($C_{31}H$, br, 1H), 2.95 ($C_{35}H$, br, 2H), 2.76 ($C_3H$, br m, 2H), 2.31 ($C_1H$, br m, 2H), 1.30–1.85 ($C_{32}H$–$C_{34}H$, $C_2H$, br m, 8H). 13C NMR (DMSO-$d_6$, 75 MHz) δ (ppm): 170.68 ($C_{30}$), 158.01 ($C_{11}$), 153.08 ($C_{12}$), 83.39 ($C_9$), 59.65 ($C_{31}$), 46.06 ($C_3$), 29.00, 27.07 ($C_2$, $C_{34}$), 24.35 ($C_{32}$), 21.99 ($C_{33}$),19.59 ($C_1$). Cl-MS: Expected mass for $(M+H^+)/z$, 312.21. Observed, 312 (($M+H^+)/z$, 5%), 294 (($M+H^+)/z$-$H_2O$, 100%). Elemental analysis: Calculated for $[C_{13}H_{25}N_7O_2$—$(CF_3CO_2H)_{2.5}$—$(H_2O)_{20}$—$Et_2O)_{0.5}]$: C, 35.82; H, 5.26; N, 15.13; F: 21.68. Found: C, 36.12; H, 5.07; N, 14.86; F, 21.55.

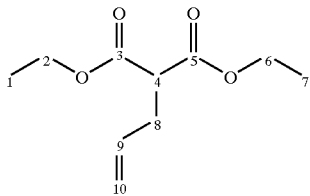

Synthesis of Compound 26

EtOH (12 mL) and sodium (0.187 g, 8.12 mMol) were stirred under $N_2$ atmosphere in a two-neck round-bottom flask (50 mL) until dissolution of the sodium. Diethyl malonate (0.95 mL, 6.24 mMol) was added to the solution, and the reaction mixture was stirred at rt for 5 min. After cooling to −50° C., allyl bromide (0.82 g, 6.87 mMol) was added dropwise. The reaction mixture was then allowed to warm to rt and was stirred overnight. The reaction was quenched with 5% aqueous $NH_4Cl$ until neutral pH, the solvents were evaporated under reduced pressure (rotavap), and the crude product was dissolved in $CH_2Cl_2$ (20 mL) and washed with $dH_2O$ (2×20 mL). The organic layer was dried over anhydrous $Na_2SO_4$, filtered, and the solvent was evaporated under reduced pressure (rotavap). Compound 26 ($C_{10}H_{16}O_4$, 0.92 g, 73%) was obtained as a colorless oil after silica gel flash chromatography (0–1.5% EA/Hex). $R_f$=0.36 (10% EA/Hex). $^1$H NMR (CDCl$_3$, 500 MHz) δ (ppm): 5.81–5.88 ($C_9H$, m, 1H), 5.0–5.88 ($C_{10}H$ m, 2H), 4.19 ($C_2H$, $C_6H$, q, J=3.4Hz, 12Hz, 4H), 2.64 ($C_4H$, t, J=6.9Hz, 1H), 1.26 ($C_7H$, t, J=9.56Hz, 6H).

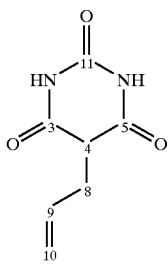

Synthesis of Compound 27

EtOH (1 L) and sodium (12.83 g, 558 mMol) were stirred in a single-neck round-bottom flask (2 L) under $N_2$ until dissolution of the sodium. To this solution urea (27.9 g, 465 mMol) and compound 27 (93.0 g, 465 mMol) were added, and the mixture was refluxed for 5 h. After cooling to rt, the reaction was quenched with 1M HCl until neutral pH. The precipitate formed was filtered and washed with EtOH (50 mL) and $Et_2O$ (50 mL), and dried under vacuum to yield compound 27 ($C_9H_{10}N_2O_3$, 52.0 g, 67%) as a white solid. $^1$H NMR (DMSO-$d_6$, 200 MHz) δ (ppm): 9.41 ($C_{11}NH$, s, 2H), 6.26–6.30 ($C_9H$, m, 1H), 5.06–5.33 ($C_{10}H$, m, 2H), 3.21 ($C_8H$, d, J=8.0Hz, 2H).

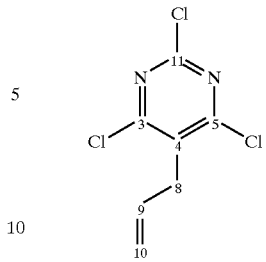

Synthesis of Compound 28

A solution of compound 27 (47.0 g, 280 mMol) and $POCl_3$ (208 mL, 223 mMol) was heated to 70° C. in a single neck round-bottom flask (500 mL), and N,N-dimethyl aniline (9.68 g, 76.5 mMol) was added dropwise. The mixture was refluxed for 4 h under $N_2$ atmosphere, then cooled to rt. Excess $POCl_3$ was removed under reduced pressure (rotavap), and the slurry was slowly poured on crashed ice (500 g). The resulting aqueous mixture was extracted with $CH_2Cl_2$ (3×100 mL), the organic layers were combined and washed with brine (100 mL), dried over anhydrous $Na_2SO_4$, filtered, and evaporated under reduced pressure (rotavap). Compound 28 ($C_7H_5Cl_3N_2$, 44 g, 71%) was obtained as a crystalline solid after silica gel flash chromatography (0–2% $Et_2O$/Hex). $R_f$=0.46 (10% EA/Hex). $^1$H NMR (CDCl$_3$, 200 MHz) δ (ppm): 5.67–5.89 ($C_9H$, m, 1H), 5.0–5.2 ($C_{10}H$, m, 2H), 3.58 ($C_8H$, d, J=6.2Hz, 2H).

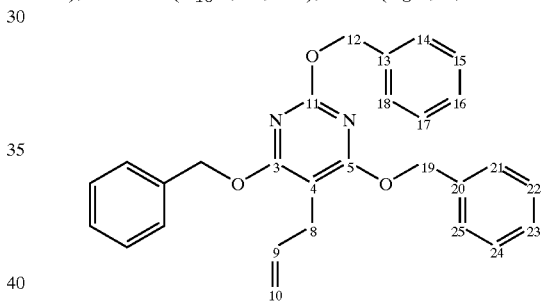

Synthesis of Compound 29

Benzyl alcohol (0.56 mL, 5.40 mMol) was added dropwise to a suspension of 95% NaH (0.134 g, 5.58 mMol) and THF (18 mL) in a two-neck round-bottom flask (1 L) under $N_2$ atmosphere. After cooling to 0° C. (ice bath) compound 28 (0.20 g, 0.9 mMol) was added in one portion, and the reaction mixture was refluxed overnight. The reaction was then quenched with 5% aqueous $NH_4Cl$ until neutral pH. After adding brine (200 mL), the mixture was extracted with EA (2×20 mL), the organic layers were combined, dried over anhydrous $Na_2SO_4$, filtered, and the solvent was evaporated under reduced pressure (rotavap). Compound 29 ($C_{28}H_{26}N_2O_3$, 0.30 g, 77%) was obtained as a white solid after silica gel flash chromatography (0–1.5% EA/Hex). $R_f$=0.50 (15% EA/Hex). mp=76–77° C. $^1$H NMR (CDCl$_3$, 200 MHz) δ (ppm): 7.21–7.44 ($CH_{14}$–$C_{18}H$, $C_{21}H$–$C_{25}H$, m, 15H), 5.74–5.95 ($C_9H$, m, 1H), 5.41 ($C_{12}H$, $C_{19}H$, br, J=4.6Hz, 6H), 4.90–5.05 ($C_{10}H$, m, 2H), 3.33 ($C_8H$, d, 2H, J=3.3Hz). $^{13}$C NMR (CDCl$_3$, 50 MHz) δ (ppm): 169.54 ($C_3$, $C_5$), 162.52 ($C_{11}$), 137.51, 135.96 ($C_9$, $C_{13}$, $C_{20}$), 128.95–127.98 ($C_{14}$–$C_{18}$, $C_{21}$–$C_{25}$), 115.45 ($C_{10}$), 96.86 ($C_4$), 69.52 ($C_{12}$), 69.18 ($C_{19}$), 27.42 ($C_8$). Cl-MS: Expected mass for (M+H$^+$)/z, 439.20. Observed, 439 ((M+H$^+$)/z, 100%). Positive high resolution FAB-MS (NBA, KIPEG): Expected mass for (M+H$^+$)/z, 439.2022. Observed, 439.2027.

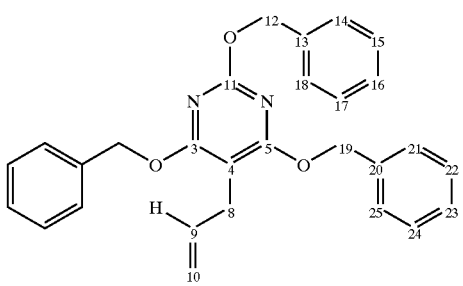

Synthesis of Compound 30

Compound 29 (10.0 g, 22.83 mMol), dioxane (200 mL), dH$_2$O (50 mL), NaIO$_4$ (14.59 g, 1.14 mMol), OsO$_4$ (0.1 M in t-BuOH, 2.23 mL, 0.114 mMol) were stirred in a single neck round-bottom flask (500 mL) overnight under N$_2$ atmosphere. The reaction was quenched with a 3% aqueous solution of sodium sulfite until the solution turned colorless. The off-white precipitate formed was dissolved in EA (200 mL) and washed with dH$_2$O (3×200 mL) and brine (100 mL). The organic layer was separated, dried over anhydrous Na$_2$SO$_4$, filtered, and the solvent was evaporated under reduced pressure (rotavap). Compound 30 (C$_{27}$H$_{24}$N$_2$O$_4$, 7.30 g, 73%), was obtained as a white solid after silica gel flash chromatography (5–25% EA/Hex). R$_f$=0.31 (15% EA/Hex). mp=81–82° C. $^1$H NMR (CDCl$_3$, 200 MHz) δ (ppm): 9.63 (C$_9$H, s, 1H), 7.33–7.52 (C$_{14}$H–C$_{18}$H, C$_{21}$H–C$_{25}$H, m, 15H), 5.43 (C$_{12}$H, C$_{20}$H, s, 6H), 3.62 (C$_8$H, s, 2H). $^{13}$C NMR (CDCl$_3$, 75 MHz) δ (ppm): 198.81 (C$_9$), 169.27 (C$_3$, C$_5$), 136.80 (C$_{12}$), 136.50 (C19), 128.28 (C$_{15}$, C$_{17}$, C$_{22}$, C$_{24}$), 127.84 (C$_{16}$, C$_{23}$), 127.40 (C$_{14}$, C$_{18}$, C$_{21}$, C$_{25}$), 89.49 (C$_4$), 69.21 (C$_{12}$), 68.77 (C$_{19}$), 37.03 (C$_8$). Cl-MS: Expected mass for (M+H$^+$)/z, 441.18. Observed, 441 ((M+H$^+$)/z, 100%). Positive high resolution FAB-MS (NBA, KIPEG): Expected mass for (M+H$^+$)/z, 441.1820. Observed, 441.1814.

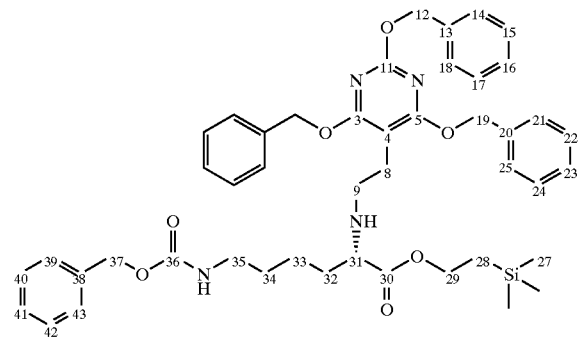

Synthesis of Compound 31

Compound 30 (0.26 g, 0.60 mMol) and Na(AcO)$_3$BH (0.19 g, 0.91 mMol) were added in one portion to a vigorously stirred solution of L-15 (0.30 g, 0.60 mMol), 1,2-DCE (5 mL) and Et$_3$N (0.12 mL, 0.65 mMol) in a single neck round-bottom flask (100 mL). The reaction mixture was stirred overnight at rt under N$_2$ atmosphere then quenched with 5% aqueous NaHCO$_3$ (2 mL). CH$_2$Cl$_2$ (30 mL) was added and the organic layer was separated and washed with 5% aqueous NaHCO$_3$ (3×30 mL) and brine (30 mL), dried over anhydrous Na$_2$SO$_4$, filtered, and evaporated under reduced pressure (rotavap). Compound 31 (C$_{46}$H$_{56}$N$_4$O$_7$Si, 0.38 g, 55%) was obtained as a foam after silica gel flash chromatography (5–15% EA/Hex). R$_f$=0.44 (30% EA/Hex). $^1$H NMR (CDCl$_3$, 200 MHz) δ (ppm): 7.24–7.51 (C$_{21}$H–C$_{25}$H, C$_{14}$H–C$_{18}$H, C$_{39}$H–C$_{43}$H, m, 20H), 5.38 (C$_{19}$H, s, 4H,), 5.13 (C$_{12}$H, s, 2H), 5.11 (C$_{37}$H, s, 2H), 4.95 (C$_{35}$NH, br, m, 1H), 4.17 (C$_{29}$H, t, J=8.6Hz, 2H), 3.40–3.00 (C$_{31}$H, C$_{35}$H, m, 3H), 2.90–2.60 C$_8$H, C$_9$H, m, 4H), 1.90–1.20 (C$_{32}$H–C$_{34}$H, m, 6H), 0.97 (C$_{28}$H, t, J=8.6Hz, 2H), 0.07 (C$_{27}$H, s, 9H). $^{13}$C NMR (CDCl$_3$, 50 MHz) δ (ppm): 175.25 (C$_{30}$) 169.19 (C$_3$, C$_5$), 161.73 (C$_{11}$), 156.26 (C$_{36}$), 136.87, 136.78, 136.59 (C$_{38}$, C$_{13}$, C$_{20}$), 128.35, 128.28, 127.95, 127.88, 127.81, 127.72, 127.40, 126.96 (C$_{14}$–C$_{18}$, C$_{21}$–C$_{25}$, C$_{39}$–C$_{43}$), 95.73 (C$_4$), 68.83 (C$_{12}$), 68.09 (C$_{19}$), 66.34 (C$_{37}$), 62.68 (C$_{29}$), 61.05 (C$_{31}$), 46.71 (C$_9$), 40.68 (C$_{35}$), 32.72 (C$_{32}$), 29.51 (C$_{34}$), 22.72 (C$_8$, C$_{33}$), 17.31 (C$_{28}$), −1.50 (C$_{27}$). PD-MS: Expected mass for (M+H$^+$)/z, 805.40. Observed, 805. Positive high resolution FAB-MS (NBA, KIPEG): Expected mass for (M+H$^+$)/z, 805.3997. Observed, 805.3984.

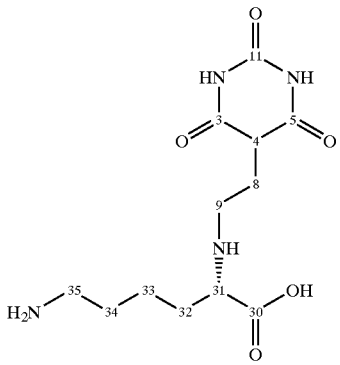

Synthesis of L-module 3

Compound 31 (0.25 g, 0.31 mMol) and 94% TFA/thioanisole (10 mL) were stirred in a single neck round-bottom flask (50 mL) for 96 h at rt under N$_2$ atmosphere. The TFA was evaporated, and the crude product was suspended in Et$_2$O (20 mL), centrifuged down (5000 rpm, 10 min), and the solid isolated was resuspended in Et$_2$O (9 mL). This suspension/centrifugation/isolation procedure was repeated three times. After drying under vacuum, L-module 3 (C$_{12}$H$_{20}$N$_4$O$_5$—(CF$_3$CO$_2$H)$_2$—(H$_2$O)$_{1.0}$—_Et$_2$O)$_{0.25}$], 0.11 g, 65%) was obtained as an off-white hygroscopic solid. $^1$H NMR (CDCl$_3$, 200 MHz) δ (ppm): 9.69 (C$_3$NH, C$_5$NH br s, 2H), 7.75 (C$_{35}$NH, br s, 3H), 2.75–3.11 (C$_9$H, C$_{35}$H, m, 4H), 2.52 (C$_8$H, m, 1.31–1.97 (C$_{32}$H–C$_{34}$H, C$_{38}$H, m, 6H). $^{13}$C NMR (CDCl$_3$, 75 MHz) δ (ppm): 171.76 (C$_{30}$) 166.34 (C$_3$, C$_5$), 152.15 (C$_{11}$), 100.23 (C$_4$), 59.68 (C$_7$), 48.43 (C$_5$), 32.54 (C$_{34}$), 29.38 (C$_{32}$), 27.17 (C$_8$), 22.01 (C$_{33}$). PD-MS: Expected mass for (M+H$^+$)/z, 301.14. Observed, 301.9. Positive high resolution FAB-MS (NBA, KIPEG): Expected mass for (M+H$^+$)/z, 301.1512. Observed, 301.1526. Elemental analysis: Calculated for [C$_{12}$H$_{20}$N$_4$O$_5$—(CF$_3$CO$_2$H)$_2$—(H$_2$O)$_{1.0}$—_Et$_2$O)$_{0.25}$]: C, 36.14: H, 4.73; N, 9.92. Found: C, 35.93; H, 4.38; N, 9.80.

Figure 5:
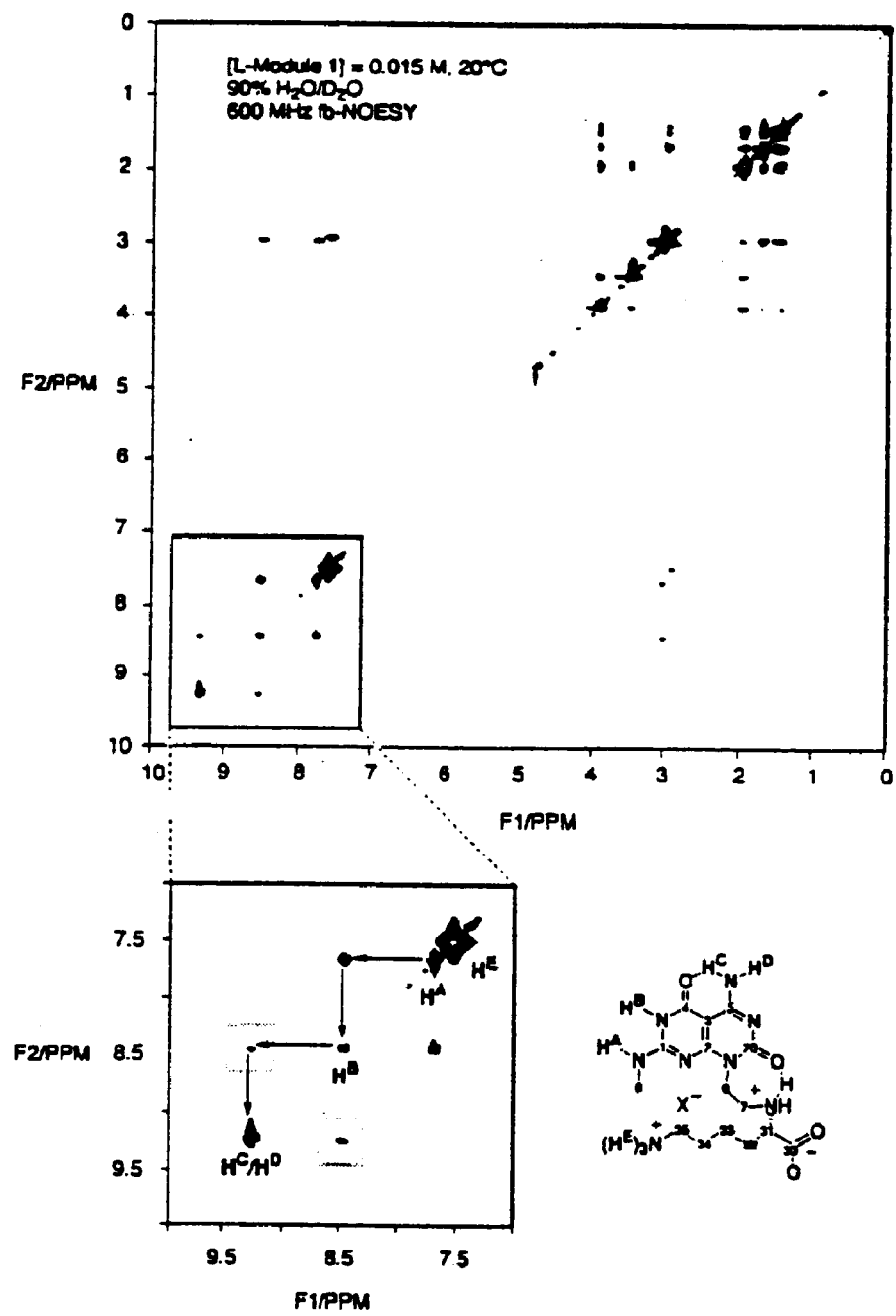
FIG. 5 is a NMR spectrum of a solution of a compound of the present invention.

Modules 2–4 were prepared to establish the role of the stacking interactions, hydrophobic effect, and the chirality of the side chain in the assembly of the tubular architectures. A shown in FIG. 5, a 600 MHz fb-NOESY 2D-$^1$H NMR spectrum of a 0.015 M solution of L-module 1 in 90% H$_2$O/D$_2$O at 20° C. and the imino/amino region of the spectrum (enlarged section) showed the formation of a six-membered supermacrocycle structure held through hydrogen bonds. In particular, L-module 1 displayed nuclear Overhauser effects (NOE's) not only between H$^A$ and H$^B$ but also between H$^B$ and H$^C$/H$^D$. Since H$^B$ and H$^C$/H$^D$ are too far apart to display any intra-modular NOE's, the observation of an NOE between them confirms the existence of inter-modular H-bonds. This result is further diagnostic of the formation of the supermacrocycle structure since no other NOE's or imino proton signals resulting from non-assembled modules or non-specific aggregates thereof were observed. The fb-NOESY (flip-back-noesy) experiment of L-module 1 was recorded in a Shigemi NMR tube on a Varian Unity Plus 600 MHz spectrometer. The States Haberkorn method was used in order to obtain a phase sensitive spectrum. A mixing time of 400 ms was used and 2×320 increments were collected with 3648 points. The data was processed using a combination of shifted sinebell and Gaussian window functions (VNMR 6.1B). Zero filling to 8 k points in $t_2$ and 2 k points in $t_1$ was applied. A spline baseline correction was applied in the acquisition dimension. The Proton assignments are as follows: 9.15 ($H^C/H^D$, br, s, 2H), 8.34 ($H^B$, br, s, 1H), 7.57 ($H^A$, br, m, 1H), 7.39 ($H^E$, br, s, 3H, protonated ammonium), 3.81 ($C_{31}H$, t, J=5.0Hz, 1H), 3.36 ($C_7H$, t, J=6.0Hz, 2H), 2.90 ($C_9H$, br, m, 3H), 2.85 ($C_{35}H$, br, m, 2H), 1.84–1.79 ($C_{32}H$, m, 2H), 1.55 ($C_{34}H$, br, s, 2H), 1.36 ($C_{33}H$, br, m, 1H), 1.29 ($C_{33}H$, br, m, 1H). $C_6H$ was suppressed with the solvent peak.

Figure 6:
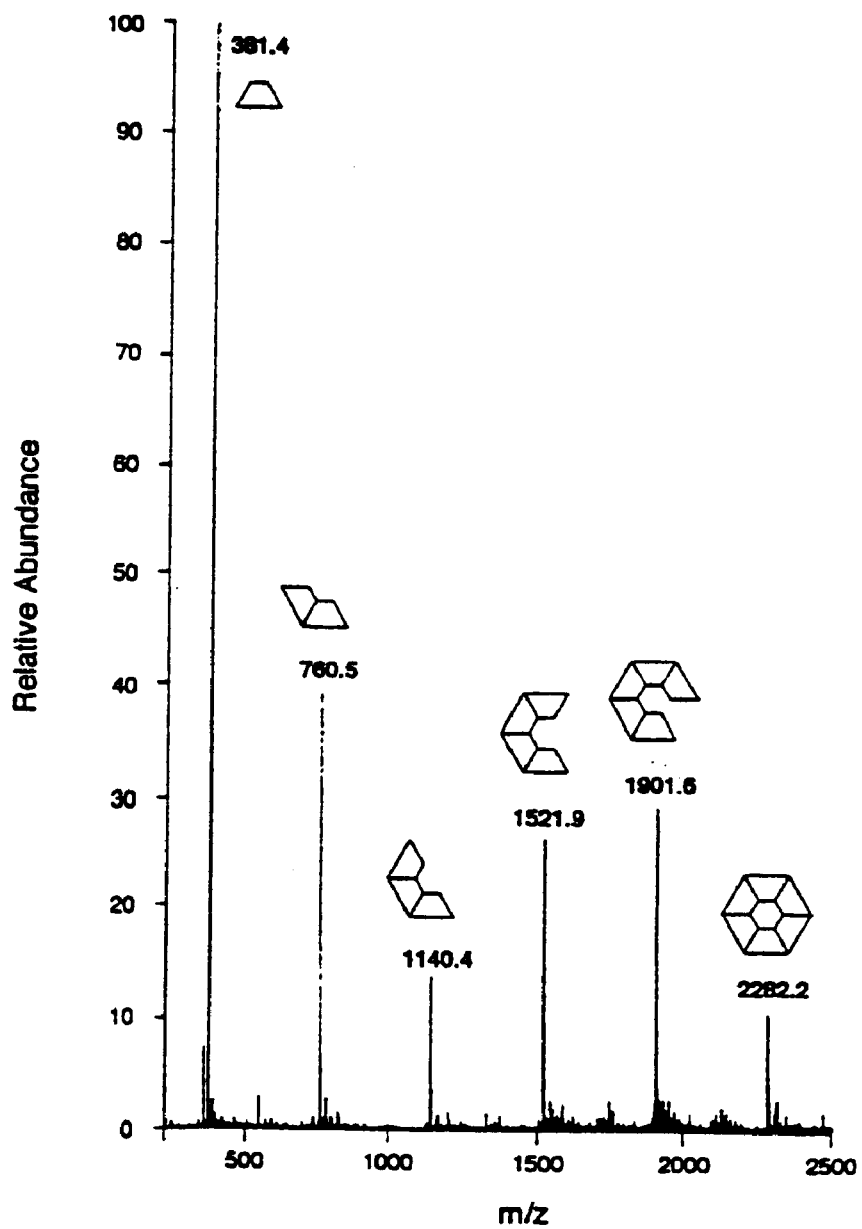
FIG. 6 is an ESI-MS spectrum of a solution of a compound of the present invention.

In agreement with the above described NMR spectrum, electrospray inonization mass spectrometry (ESI-MS) (Finnigan MATLCQ) of a 1 mM solution of L-module 1 in $CH_3OH/H_2O$ (1/1) displayed all the peaks corresponding to the non-covalent intermediate species (1-mer to 6-mer) of the parent supermacrocycle as shown in FIG. 6. In particular, the peaks at 381.4, 760.5, 1140.4, 1521.9, 1901.6 and 2282.2 correspond to the non-covalent intermediate species of the self-assembled supermacrocycle (1-mer to 6-mer). Because of their charged nature the assemblies were characterized without introducing additional ions. Under the same conditions an equimolar aqueous mixture of the L-modules 2 and 3 did not undergo self-assembly.

Figure 7:
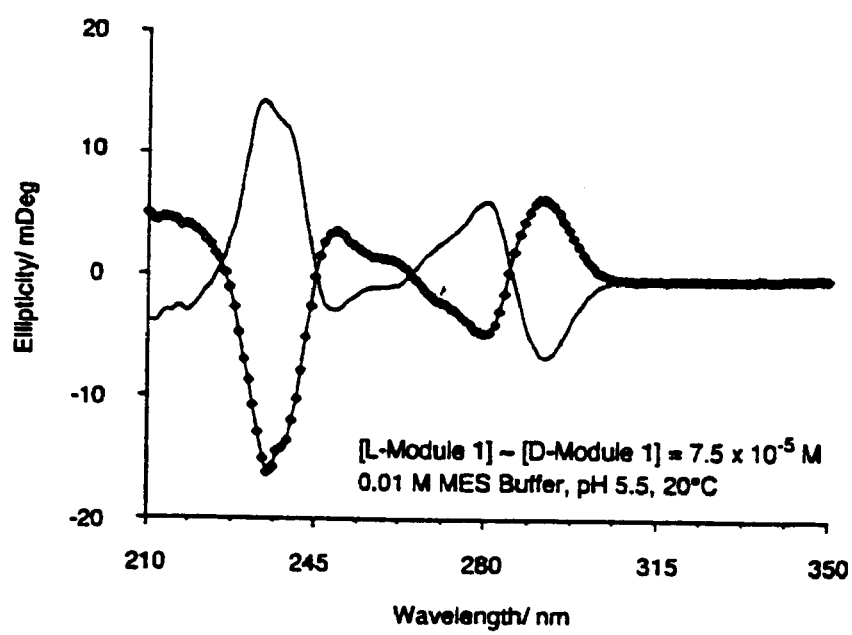
FIG. 7 is a CD spectrum of solutions of compounds of the present invention.
Figure 8:
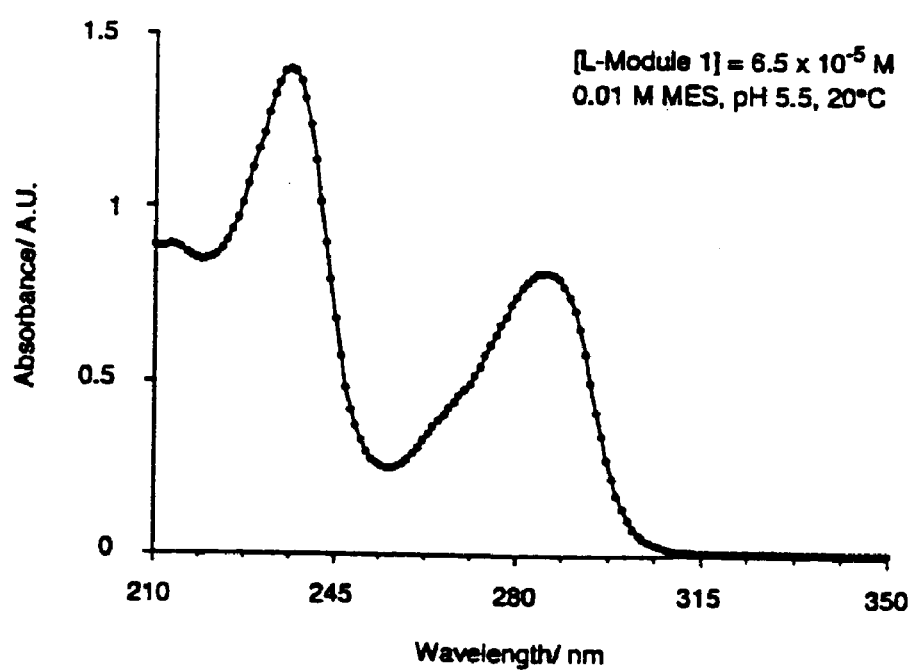
FIG. 8 is an absorbance spectrum of a solution of a compound of the present invention.

Correlation between the supramolecular chirality of foliate- and G-quadruplexes and circular dichroism (CD) activity has been drawn on the basis of exciton coupling theory. The signed order of the CD exciton couplet is governed by the relative helicity of the relevant two electric dipole transition moments, one from each stacked base. As shown in FIG. 7, the CD spectra (Jasco J-810) of L-module 1 and its D-isomer (open diamonds) in an aqueous buffered solution display a typical couplet centered at 286 nm, characteristic of stacked bases in a helical environment, that vanishes at higher temperatures. (Note MES: 2—_N-Morpholino) ethanesulfonic acid.) Under identical conditions, L-modules 2 and 3 or an equimolar mixture of both, as well as the achiral module 4 were CD-silent. Furthermore, the position of the CD couplet maxima (280 and 292 nm) are not identical to their corresponding maximum in the absorption spectrum (285 nm, see FIG. 8: $\lambda^1_{max}$=236 nm ($\epsilon$=21,500 $M^{-1}cm^{-1}$); $\lambda^2_{max}$=285 nm ($\epsilon$=12, 500 $M^{-1}cm^{-1}$), which indicates that the CD spectra are caused by chirality and not by linear dichroism of partially oriented samples. In the latter case, differently polarized absorption bands would appear as positive and negative bands in a CD spectrum, with their maxima at the same position as in the absorption spectrum. Note also that L-module 1 does not form gels or liquid crystalline phases in water. At higher concentration this material tends to precipitate out of the solution as a white solid.

Figure 9:
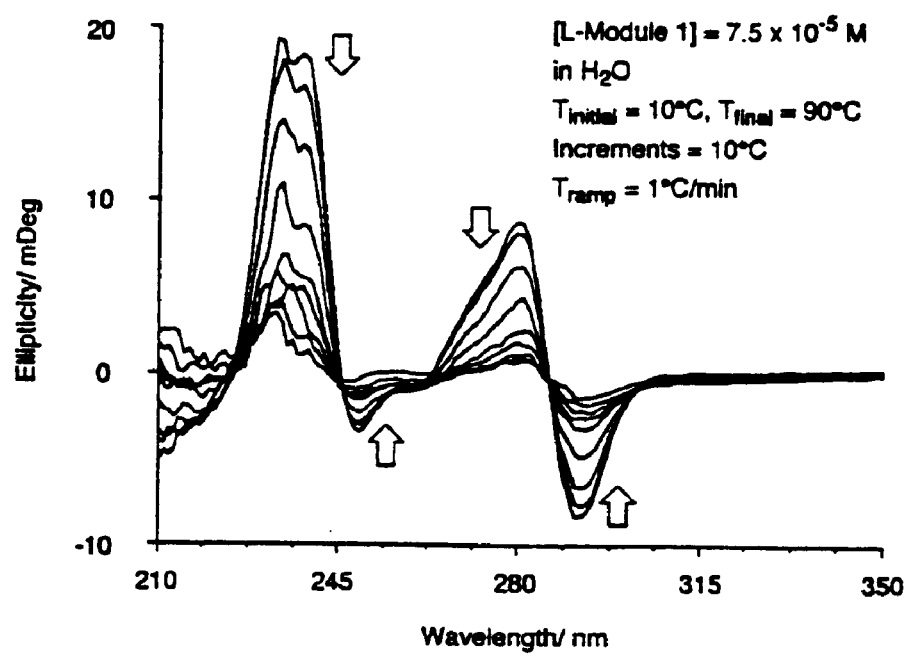
FIG. 9 is a variable temperature CD spectrum of a solution of a compound of the present invention.
Figure 10:
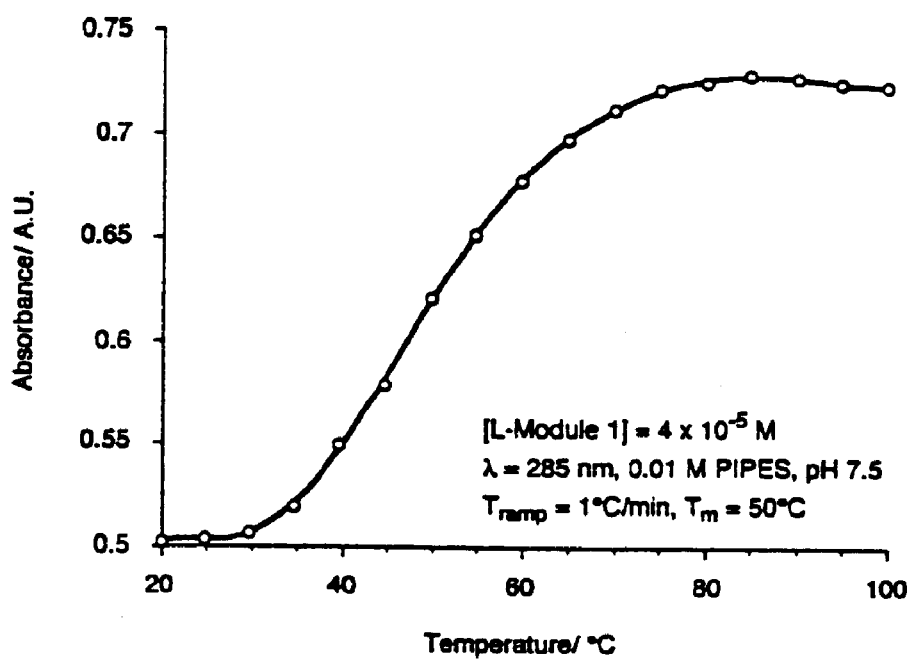
FIG. 10 is a melting curve of a solution of a compound of the present invention.

The hyperchromicity observed upon deoxyribonucleic acids (DNA) denaturation is a powerful indicator of its stability and tertiary structure. In this regard, the supramolecular outcome of L-module 1 behaves very much like DNA: The absorbance spectrum undergoes a cooperative hyperchromic effect as the temperature increases (melting temperature $T_m^{285\ nm}$=50° C.). The same transition was recorded by variable temperature CD ($\lambda$=292 nm). In particular, as shown in FIG. 9, the disappearance of the CD peaks at higher temperatures demonstrates that the recorded cotton effect is the result of supramolecular chirality rather than intrinsic molecular chirality of L-module 1. Also, the observation of several isosbectic points (224, 246, 286, 303 nm) is an indication that the melting transition in water takes place between two main stable species (nanotube ⇔ [supermacrocycle]# ⇔ monomeric modules). A plot of the elliptcity at 291 nm as a function of temperature yields a cooperative melting transition around 50° C., in agreement with the transition recorded in the absorbance mode as shown in FIG. 10. In particular, FIG. 10 shows a Melting curve of 5×10⁻⁵ M solution of L-module 1 in 0.01 M PIPES, pH 7.5. $\lambda$=285 nm, $T_{ramp}$=1° C./min. $T_m$=50° C. The wide transition temperature (from 35° to 70° C.) is presumably due to the length polydispersity of the sample.

In combination with NMR, ESI-MS, and CD it is clear that: (a) L-module 1 undergoes a cooperative, hierarchical self-assembly process through H-bonding, stacking interactions and hydrophobic effects and (b) the assembly generated displays supramolecular chirality, as a result of helically stacked supermacrocycles.

Figure 11:
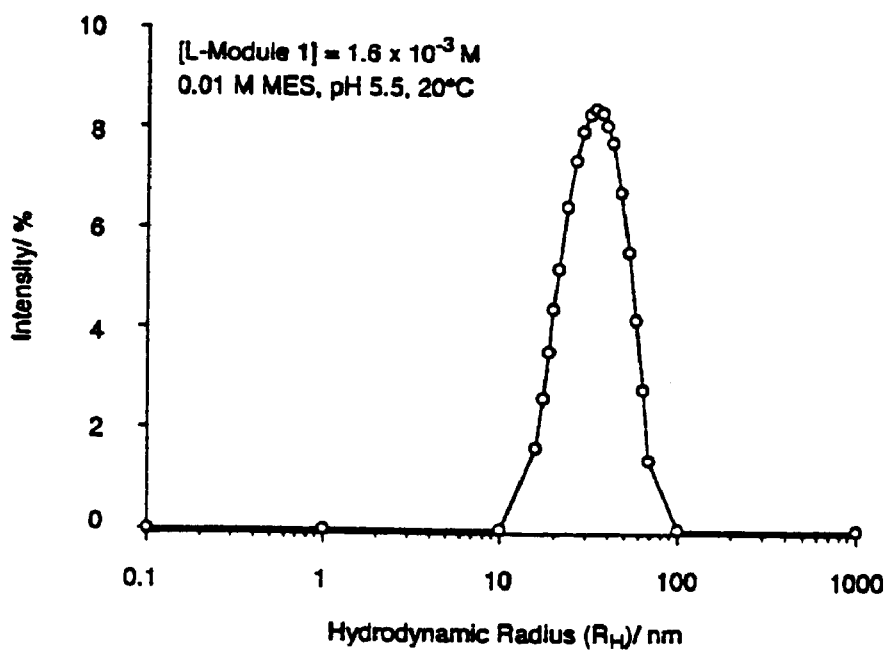
FIG. 11 is a dynamic light scattering regularization diagram of a a solution of a compound of the present invention.

To assess the size of the assemblies generated, the dynamic light scattering (DLS) spectrum was recorded for a buffered solution of L-module 1. As specifically shown in FIG. 11, the dynamic light scattering regularization diagram (Protein-Solutions $MSTC_{200}$) of a 1.0 mg/ml solution of L-module 1 in 0.01 M MES buffer, pH 5.5, 20° C. showed an average hydrodynamic radius of 30.4 nm (average of 15 measurments). The narrow distribution (92% in the range 19–69 nm) obtained with an average apparent hydrodynamic radius, RH, Of 30.4 nm is rationalized by invoking a columnar stack reminiscent of the solid or liquid crystalline states of folate- and G-quadruplexes, and other self-assembled materials. As control experiments, L-modules 2, 3, or an equimolar mixture of both did not generate any detectable aggregate.

Figure 12:
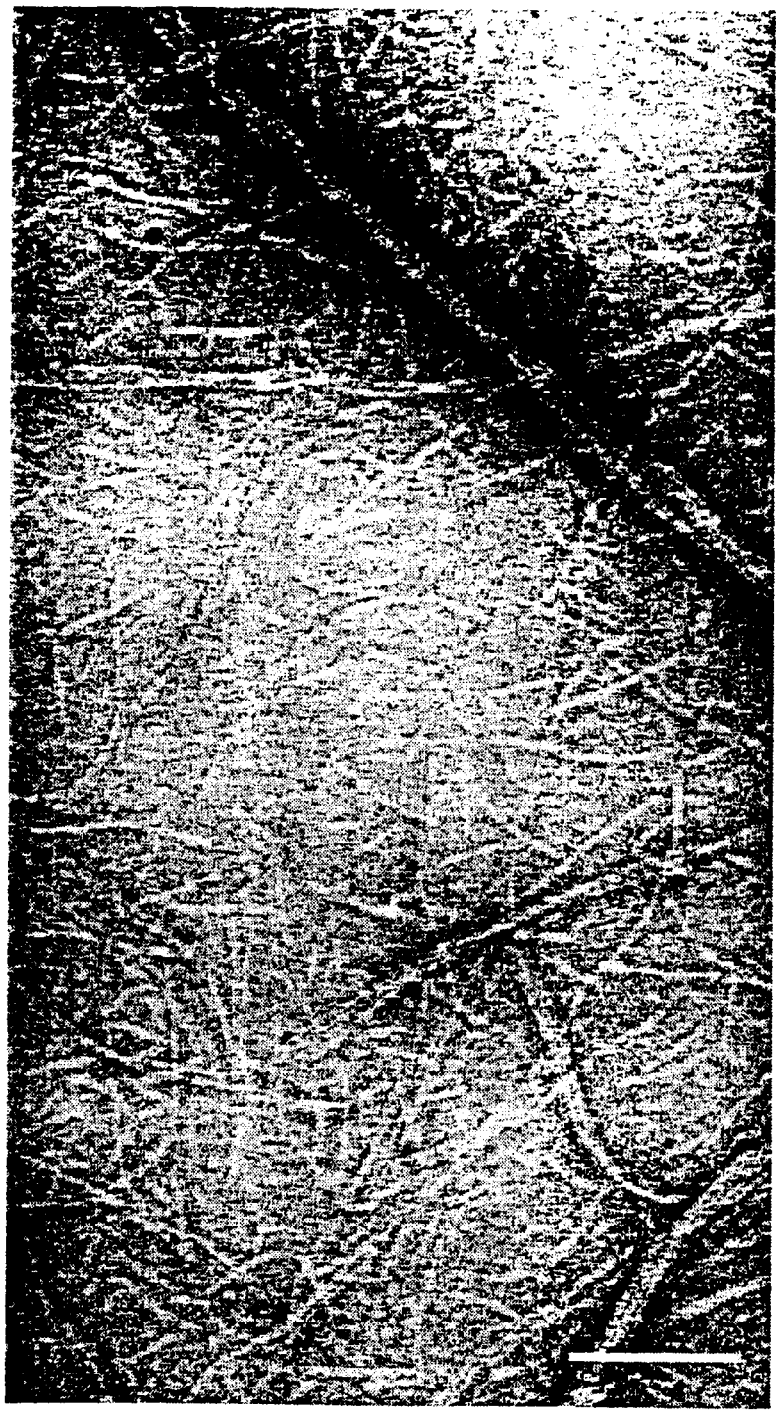
FIG. 12 is a large area transmission electron micrograph of nanotubes of the present invention.

Transmission electron micrograph (TEM) provided visual evidence of the formation of the nanotubular assemblies and confirmation of the spectroscopic data discussed above. FIG. 12 is a large area transmission electron micrograph of a negatively stained sample of L-module 1 (scale bare=100 nm). Formvar and carbon coated grids were floated on droplets of 0.5 mg/ml in 0.01 M MES buffer at pH 5.5 for ~30 s, transferred to droplets of 2% aqueous uranyl acetate for ~30 s, blotted and viewed in a Philips EM-400 transmission electron microscope at 80 kV and 60,000× magnification. Images of the 8.75 nm lattice spacing of catalase crystals, taken at the same magnification, were used for calibration. Negatives were scanned into a computer at 1600 dpi resolution and the diameter of nanotubes was determined using the image analysis program IP Lab (Scanalytics, Fairfax, Va.). The measured outer diameter of ~4.0 nm (this number includes a layer of the staining agent) is an average of 200 measurements made on randomly selected nanotubes. In agreement with the DLS data, most of the sample's length revolves around ~60 nm. Although ~10% of the sample forms bundles, there are no higher order twisted or helical aggregates, thereby suggesting that the CD spectra recorded are the result of an intrinsic property of each individual nanotube. Since they are undetectable by DLS and because the sample was filtered on 0.2 $\mu$m filters prior to TEM imaging, the nanotube bundles observed arise most likely during solvent evaporation on the TEM grid.

It should be understood that the above described system establishes that electrostatic, stacking and hydrophobic interactions can be effectively orchestrated by hydrogen bonds to direct the hierarchical assembly and organization of helical nanotubular architectures in an aqueous milieu. Furthermore, utilizing the above discussed synthetic strategy a wide variety of structurally different modules (i.e. molecules) can be synthesized. Including but not limited to, for example, a compound having the formula:

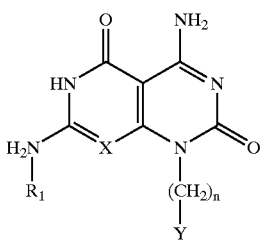

wherein X is carbon or nitrogen; n is an integer of, 1, 2, 3, or 4; Y is an amino acid having an amino group covalently bound to an α-carbon of said amino acid and said amino group is covalently bound to a carbon of the $(CH_2)_n$ group; and $R_1$ is aliphatic; and salts thereof: a compound having the formula:

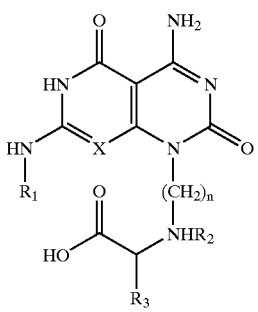

wherein X is carbon or nitrogen; n is an integer of 1, 2, 3, or 4; $R_1$ is aliphatic; $R_2$ is hydrogen; and $R_3$ is —$C_3$, —$CH_2OH$, —$CH_2CH_2SCH_3$, —$CH_2CO_2H$, —$CH_2CH(CH_3)_2$, —$CH_2C_6H_5$, —$CH_2$-p-$(OH)C_6H_4$, —$CH_2CH_2CH_2CH_2NH_2$, or $R_2$ and $R_3$ together form

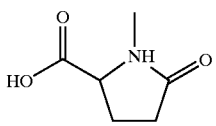

and salts thereof; and a compound having the formula:

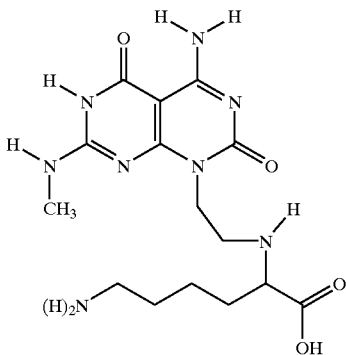

and salts thereof.

It should also be understood that the above described modules can be utilized in a method for forming nanotubes. In particular, the modules of the present invention self assembly into nanotubes upon disposing the same in an aqueous solution at an appropriate concentration, for example in a pH 5.5 MES buffer at an appropriate concentration at 20° C. Furthermore, as previously mentioned it should be appreciated that having the ability to oligomerize and/or functionalize the modules at virtually any position greatly enhances the ability to form a wide range of structurally unique modules and thus easily form a wide range of nanotubes with specifically desired physical/chemical characteristics. The exact conditions for forming nanotubes with any one, or combination of, the various modules of the present invention will depend upon the particular characteristics of the module/modules utilized. However, in light of the above disclosure these conditions are easily determinable by one of ordinary skill in the art from only routine experimentation.

While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected.

What is claimed is:

1. A compound having the formula:

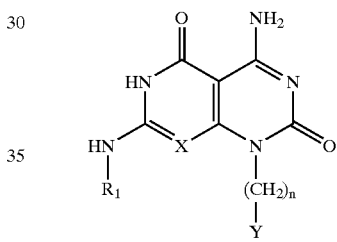

wherein X is CH or nitrogen; n is an integer of, 1, 2, 3, or 4; Y is an amino acid having an amino group covalently bound to an α-carbon of said amino acid and said amino group is covalently bound to a carbon of the $(CH_2)_n$ group; and $R_1$ is aliphatic; and salts thereof.

2. The compound of claim 1, wherein:

said amino acid is alanine, arginine, asparagine, aspartate, cysteine, glutamine, glutamate, glycine, histidine, isoleucine, leucine, lysine, methionine, phenylalanine, proline, serine, threonine, tryptophan, tyrosine, valine, hydroxyproline, γ-carboxyglutamate, or o-phosphoserine.

3. The compound of claim 1, wherein:

$R_1$ is alkyl.

4. The compound of claim 3, wherein:

$R_1$ is $CH_3$.

5. The compound of claim 1, wherein:

n is 2.

6. The compound of claim 1, wherein:

X is N, and

N is 2.

7. The compound of claim 6, wherein:

Y is lysine.

8. The compound of claim 7, wherein:

$R_1$ is $CH_3$.

9. A compound having the formula:

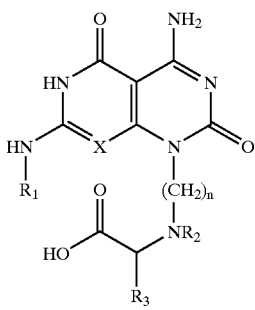

wherein X is CH or nitrogen; n is an integer of 1, 2, 3, or 4; $R_1$ is aliphatic; $R_2$ is hydrogen; and $R_3$ is —$CH_3$, —$CH_2OH$, —$CH_2CH_2SCH_3$, —$CH_2CO_2H$, —$CH_2CH(CH_3)_2$, —$CH_2C_6H_5$, —$CH_2$-p-$(OH)C_6H_4$, —$CH_2CH_2CH_2CH_2NH_2$, or $R_2$ and $R_3$ together form

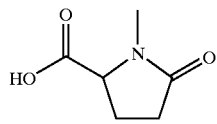

and salts thereof.

10. The compound of claim 9, wherein:
$R_1$ is alkyl.
11. The compound of claim 10, wherein:
$R_1$ is $CH_3$.
12. The compound of claim 9, wherein;
n is 2,
X is N, and
$R_3$ is —$CH_2CH_2CH_2CH_2N_2$.
13. A method of forming a nanotube, comprising:
(a) disposing a compound having the formula

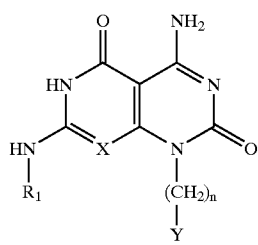

or salts thereof in a solution at a sufficient concentration so that said nanotube is formed, wherein X is CH or nitrogen; n is an integer of, 1, 2, 3, or 4; Y is an amino acid having an amino group covalently bound to an α-carbon of said amino acid and said amino group is covalently bound to a carbon of the $(CH_2)_n$ group; and $R_1$ is aliphatic.

14. The method of claim 13, wherein:
(a) includes (i) molecules of said compound self-assembling into a number of supermacrocycle structures and (ii) a number of said supermacrocycle structures self-assembling to form said nanotube.
15. The method of claim 14, wherein:
said supermacrocycle structure is a 6-mer.
16. The method of claim 13, wherein:
(a) includes disposing said compound in an aqueous solution.

17. The method of claim 13, wherein:
said amino acid is alanine, arginine, asparagine, aspartate, cysteine, glutamine, glutamate, glycine, histidine, isoleucine, leucine, lysine, methionine, phenylalanine, proline, seine, threonine, tryptophan, tyrosine, valine, hydroxyproline, γ-carboxyglutamate, or o-phosphoserine.
18. The method of claim 13, wherein:
$R_1$ is alkyl.
19. The method of claim 18, wherein:
$R_1$ is $CH_3$.
20. The method of claim 13, wherein:
X is N, and
N is 2.
21. The method of claim 20, wherein:
Y is lysine.
22. The method of claim 21, wherein:
$R_1$ is $CH_3$.
23. A method of forming a nanotube, comprising:
(a) disposing a compound having the formula

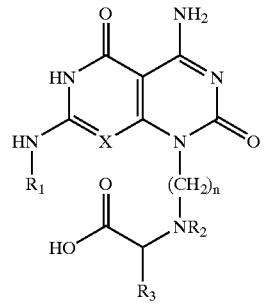

or salts thereof in a solution at a sufficient concentration so that said nanotube is formed, wherein X is CH or nitrogen; n is an integer of 1, 2, 3, or 4; $R_1$ is aliphatic; $R_2$ is hydrogen; and $R_3$ is —$CH_3$, —$CH_2OH$, —$CH_2CH_2SCH_3$, —$CH_2CO_2H$, $CH_2CH(CH_3)_2$, —$CH_2C_6H_5$, —$CH_2$-p-(OH)$C_6H_4$, —$CH_2CH_2CH_2CH_2NH_2$, or $R_2$ and $R_3$ together form

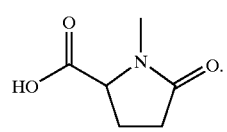

24. The method of claim 23, wherein:
$R_1$ is alkyl.
25. The method of claim 24, wherein:
$R_1$ is $CH_3$.
26. The method of claim 23, wherein:
n is 2,
X is N, and
$R_3$ is —$CH_2CH_2CH_2CH_2NH_2$.
27. The method of claim 23, wherein:
(a) includes (i) molecules of said compound self-assembling into a number of supermacrocycle structures and (ii) a number of said supermacrocycle structures self-assembling to form said nanotube.
28. The method of claim 27, wherein:
said supermacrocycle structure is a 6-mer.
29. The method of claim 23, wherein:
(a) includes disposing said compound in an aqueous solution.

30. A compound having the formula:

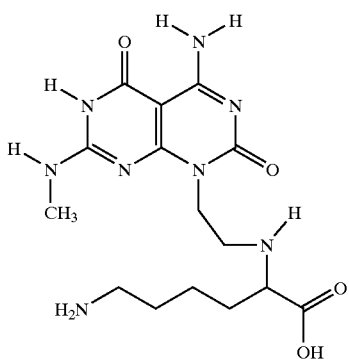

and salts thereof.

31. A method of forming a nanotube, comprising:
(a) disposing a compound having the formula

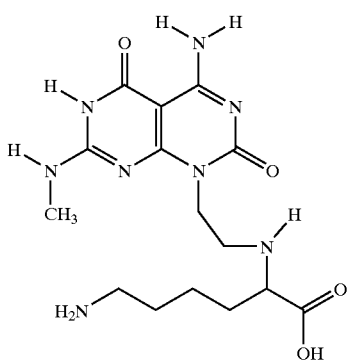

in a solution at a sufficient concentration so that said nanotube is formed.

32. The method of claim 31, wherein:
(a) includes (i) molecules of said compound self-assembling into a number of supermacrocycle structures and (ii) a number of said supermacrocycle structures self-assembling to form said nanotube.

33. The method of claim 32, wherein:
said supermacrocycle structure is a 6-mer.

34. The method of claim 31, wherein:
(a) includes disposing said compound in an aqueous solution.

35. A nanotube, comprising:
molecules having the formula

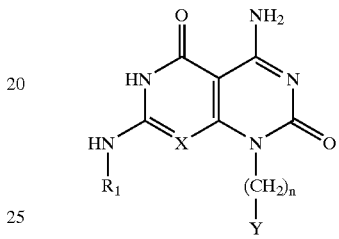

wherein X is CH or nitrogen; n is an integer of, 1, 2, 3, or 4; Y is an amino acid having an amino group covalently bound to an α-carbon of said amino acid and said amino group is covalently bound to a carbon of the $(CH_2)_n$ group; and $R_1$ is aliphatic; and salts thereof, and a number of said molecules are arranged relative to one another so as to form a supermacrocycle.

* * * * *